United States Patent
Lightfoot et al.

(10) Patent No.: US 12,378,291 B2
(45) Date of Patent: *Aug. 5, 2025

(54) METHOD FOR THE TREATMENT OF ALLERGIC RHINITIS

(71) Applicant: Revolo Biotherapeutics Limited, Cambridgeshire (GB)

(72) Inventors: Andrew Lightfoot, Cambridgeshire (GB); Nicola Cooper, Cambridgeshire (GB); Donata Federici Canova, Cambridgeshire (GB)

(73) Assignee: Revolo Biotherapeutics Limited, Great Shelford (GB)

(*) Notice: Subject to any disclaimer, the term of this patent is extended or adjusted under 35 U.S.C. 154(b) by 0 days.

This patent is subject to a terminal disclaimer.

(21) Appl. No.: 18/528,697

(22) Filed: Dec. 4, 2023

(65) Prior Publication Data

US 2024/0317821 A1    Sep. 26, 2024

Related U.S. Application Data

(63) Continuation of application No. 17/751,313, filed on May 23, 2022, now Pat. No. 11,834,478, which is a continuation of application No. 16/476,058, filed as application No. PCT/GB2018/050073 on Jan. 11, 2018, now Pat. No. 11,479,585.

(30) Foreign Application Priority Data

Jan. 12, 2017  (GB) ..................... 1700555

(51) Int. Cl.
*A61K 39/00* (2006.01)
*A61K 45/06* (2006.01)
*C07K 14/35* (2006.01)
*A61K 38/00* (2006.01)

(52) U.S. Cl.
CPC .............. *C07K 14/35* (2013.01); *A61K 45/06* (2013.01); *A61K 38/00* (2013.01)

(58) Field of Classification Search
CPC .................................................. C07K 14/35
See application file for complete search history.

(56) References Cited

U.S. PATENT DOCUMENTS

| | | | |
|---|---|---|---|
| 9,085,632 B2 | 7/2015 | Coates et al. | |
| 11,479,585 B2 | 10/2022 | Lightfoot et al. | |
| 11,834,477 B2 * | 12/2023 | Bryan | C07K 14/35 |
| 11,834,478 B2 * | 12/2023 | Lightfoot | A61P 19/02 |
| 2006/0217407 A1 | 9/2006 | Redkar et al. | |
| 2011/0052616 A1 | 3/2011 | Coates et al. | |
| 2014/0341932 A1 | 11/2014 | Coates et al. | |
| 2020/0369750 A1 | 11/2020 | Kawakami et al. | |
| 2021/0230233 A1 | 7/2021 | Lightfoot et al. | |
| 2021/0371475 A1 | 12/2021 | Bryan | |
| 2022/0024995 A1 | 1/2022 | Bryan | |
| 2022/0281929 A1 | 9/2022 | Lightfoot et al. | |

FOREIGN PATENT DOCUMENTS

| | | |
|---|---|---|
| CN | 1735427 A | 2/2006 |
| CN | 101965361 A | 2/2011 |
| CN | 102573896 A | 7/2012 |
| JP | 2004513925 A | 5/2004 |
| JP | 2007503382 A | 2/2007 |
| JP | 2010502765 A | 1/2010 |
| JP | 2011513215 A | 4/2011 |
| JP | 2013510094 A | 3/2013 |
| JP | 2014532395 A | 12/2014 |
| JP | 2020504161 A | 2/2020 |
| JP | 7252895 B2 | 3/2023 |
| WO | 0240037 A2 | 5/2002 |
| WO | 0240038 A2 | 5/2002 |
| WO | 2005021043 A2 | 3/2005 |
| WO | 2008033820 A2 | 3/2008 |
| WO | 2009106819 A2 | 9/2009 |
| WO | 2011057078 A2 | 5/2011 |
| WO | 2013057499 A1 | 4/2013 |
| WO | 2018130834 A1 | 7/2018 |
| WO | 2018130835 A1 | 7/2018 |

OTHER PUBLICATIONS

"International Search Report and Written Opinion received for PCT Patent Application No. PCT/GB2018/050073 mailed Jun. 22, 2018", 22 pages.
Brightling, "Clinical trial research in focus: do trials prepare US to deliver precision medicine in those with severe asthma?", Lancet Respiratory Medicine, vol. 05, Feb. 2017, pp. 92-95.
Coin, et al., "Solid-phase peptide synthesis: from standard procedures to the synthesis", Nature Protocols, vol. 2, No. 12, 2007, pp. 3247-3256.
Derossi, et al., "Trojan peptides: the penetratin system for intracellular delivery", Trends in Cell Biology, vol. 8, Feb. 1998, pp. 84-87.
Fields, et al., "Solid phase peptide synthesis utilizing 9-fluorenylmethoxycarbonyl amino acids", Int. J. Peptide Protein Res., vol. 35, 1990, pp. 161-214.
Heidari, Behzad, "Rheumatoid Arthritis: Early Diagnosis and Treatment Outcomes", Caspian Journal of Internal Medicine, vol. 2, Issue 1, 2011, pp. 161-170.
Hein, Jotun, "Unified Approach to Alignment and Phylogenies", Methods in Enzymology, vol. 183,, 1990, pp. 626-645.

(Continued)

*Primary Examiner* — Albert M Navarro
(74) *Attorney, Agent, or Firm* — Adler Pollock & Sheehan P.C.; Michel Morency

(57) ABSTRACT

The present invention relates to a method for the acute treatment of a relapsing-remitting condition, the method comprising the step of administering to a subject in need thereof one or more doses of an effective amount of a peptide molecule as defined in claim 1 in response to or during a relapse, wherein the method causes remission of the condition.

21 Claims, 12 Drawing Sheets

Specification includes a Sequence Listing.

(56) References Cited

OTHER PUBLICATIONS

Jones, J. H., "A Short Guide to Abbreviations and Their Use in Peptide Science", Journal of Peptide Science, vol. 5, 1999, pp. 465-471.

Juniper, et al., "Development and Validation of a Questionnaire to Measure Asthma Control", European Respiratory Journal, vol. 14, 1999, pp. 902-907.

Laskey, et al., "Nucleosomes are assembled by an acidic polypeptide which binds histones and transfers them to DNA", Nature, vol. 275, Oct. 5, 1978, pp. 416-420.

McDowell, et al., "Structural Studies of Potent Constrained RGD Peptides", Journal of the American Society, vol. 114, No. 24, Nov. 18, 1992, pp. 9245-9253.

Page, et al., "PIN201104, A Peptide Derived from Mycobacterium Tuberculosis Chaperonin 60.1 Shows Prolonged Modulation of Allergic Inflammation in Murine Lungs", American Journal of Respiratory and Critical Care Medicine, 1999; A2861, 2019, 1 page.

Pavor, et al., "After Asthma: Redefining Airways Diseases", The Lancet Commissions, vol. 391, Jan. 27, 2018, pp. 350-400.

Perng, et al., "Characteristics of Airway Inflammation and Bronchodilator Reversibility in COPD", Chest, 126, vol. 2, Aug. 2004, pp. 375-381.

Ramani, et al., "Cytokines: The Good, the Bad, and the Deadly", International Journal of Toxicology, vol. 34, Issue 4, 2015, pp. 355-365.

Ranford, et al., "Chaperonins are cell-signalling proteins: the unfolding biology of molecular chaperones", Expert Reviews in Molecular Medicine, vol. 2(8), Sep. 15, 2000, pp. 1-17.

Ranson, et al., "Review Article: Chaperones", Biochem. J, vol. 333, 1998, pp. 233-242.

Saragovi, et al., "Loops and Secondary Structure Mimetics: Development and Applications in Basic Science and Rational Drug Design", Biotechnology, vol. 10, Jul. 1992, pp. 773-778.

Thompson, et al., "Clustal W: improving the sensitivity of progressive multiple sequence alignment through sequence weighting, position-specific gap penalties and weight matrix choice", Nucleic Acids Research, vol. 22, No. 22, 1994, pp. 4673-4680.

Zugel, et al., "Role of heat shock polypeptides in protection from and pathogenesis of infectious diseases", Clinical Microbiology Reviews, vol. 12, No. 1, Jan. 1999, pp. 19-39.

Fautrel, et al., "De-intensifying treatment in established rheumatoid arthritis (RA): Why, how, when and in whom can DMARDs be tapered?", Best Practice & Research Clinical Rheumatology, vol. 29, 2015, 16 pages.

Klarenbeek, et al., "Discontinuing treatment in patients with rheumatoid arthritis in sustained clinical remission: exploratory analyses from the BeSt study", Annals of Rheumatic diseases, vol. 70, 2011, pp. 315-319.

Schett, et al., "Tapering biologic and conventional DMARD therapy in rheumatoid arthritis: current evidence and future directions", Annals of Rheumatic Diseases, vol. 75, 2016, pp. 1428-1437.

International Search Report and Written Opinion for PCT Patent Application No. PCT/IB2023/000083, mailed Aug. 17, 2023, 11 pages.

International Search Report and Written Opinion for PCT Patent Application No. PCT/GB2023/051282, mailed Jun. 23, 2023, 12 pages.

International Search Report and Written Opinion for PCT Patent Application No. PCT/IB2024/000197, mailed Sep. 23, 2024, 16 pages.

Jardat, "Thirteen Decades of Peptide Synthesis: Key Developments in Solid Phase Peptide Synthesis and Amide Bond Formation Utilized in Peptide Ligation," Amino Acids, 50:39-68 (2018).

Kong, et al., "Suppression of neovascularization and experimental arthritis by D-form of anti-flt-1 peptide conjugated with mini-PEG™," Angiogenesis, 14:431-442 (2011).

* cited by examiner

SEQ ID NO:1 vs vehicle + LPS/IFNγ treatment gene expression fold change

SEQUENCE LISTING

```
Sequence total quantity: 25
SEQ ID NO: 1           moltype = AA  length = 31
FEATURE                Location/Qualifiers
REGION                 1..31
                       note = peptide molecule
source                 1..31
                       mol_type = protein
                       organism = synthetic construct
SEQUENCE: 1
DGSVVVNKVS ELPAGHGLNV NTLSYGDLAA D                                    31

SEQ ID NO: 2           moltype = AA  length = 13
FEATURE                Location/Qualifiers
REGION                 1..13
                       note = peptide molecule
VARIANT                1
                       note = MISC_FEATURE - Xaa is absent or is selected from the
                        group consisting of a beta alanine residue,
                        9-amino-3,6-dioxaoctanoic acid, and an acetyl group
source                 1..13
                       mol_type = protein
```

```
                            organism = synthetic construct
SEQUENCE: 2
XHGLNVNTLS YGD                                                              13

SEQ ID NO: 3                moltype = AA   length = 12
FEATURE                     Location/Qualifiers
REGION                      1..12
                            note = peptide molecule
SITE                        12
                            note = MISC_FEATURE - Amidated residue (NH2 group)
source                      1..12
                            mol_type = protein
                            organism = synthetic construct
SEQUENCE: 3
DGSVVVNKVS EL                                                               12

SEQ ID NO: 4                moltype = AA   length = 22
FEATURE                     Location/Qualifiers
REGION                      1..22
                            note = peptide molecule
source                      1..22
                            mol_type = protein
                            organism = synthetic construct
SEQUENCE: 4
SELPAGHGLN VNTLSYGDLA AD                                                    22

SEQ ID NO: 5                moltype = AA   length = 15
FEATURE                     Location/Qualifiers
REGION                      1..15
                            note = peptide molecule
source                      1..15
                            mol_type = protein
                            organism = synthetic construct
SEQUENCE: 5
SELPAGHGLN VNTLS                                                            15

SEQ ID NO: 6                moltype = AA   length = 12
FEATURE                     Location/Qualifiers
REGION                      1..12
                            note = peptide molecule
SITE                        12
                            note = MISC_FEATURE - Amidated residue (NH2 group)
source                      1..12
                            mol_type = protein
                            organism = synthetic construct
SEQUENCE: 6
PAGHGLNVNT LS                                                               12

SEQ ID NO: 7                moltype = AA   length = 28
FEATURE                     Location/Qualifiers
REGION                      1..28
                            note = peptide molecule
source                      1..28
                            mol_type = protein
                            organism = synthetic construct
SEQUENCE: 7
VVVNKVSELP AGHGLNVNTL SYGDLAAD                                              28

SEQ ID NO: 8                moltype = AA   length = 25
FEATURE                     Location/Qualifiers
REGION                      1..25
                            note = peptide molecule
source                      1..25
                            mol_type = protein
                            organism = synthetic construct
SEQUENCE: 8
NKVSELPAGH GLNVNTLSYG DLAAD                                                 25

SEQ ID NO: 9                moltype = AA   length = 19
FEATURE                     Location/Qualifiers
REGION                      1..19
                            note = peptide molecule
source                      1..19
                            mol_type = protein
                            organism = synthetic construct
SEQUENCE: 9
PAGHGLNVNT LSYGDLAAD                                                        19

SEQ ID NO: 10               moltype = AA   length = 16
```

```
FEATURE              Location/Qualifiers
REGION               1..16
                     note = peptide molecule
source               1..16
                     mol_type = protein
                     organism = synthetic construct
SEQUENCE: 10
HGLNVNTLSY GDLAAD                                                        16

SEQ ID NO: 11        moltype = AA  length = 16
FEATURE              Location/Qualifiers
REGION               1..16
                     note = peptide molecule
source               1..16
                     mol_type = protein
                     organism = synthetic construct
SEQUENCE: 11
DGSVVVNKVS ELPAGH                                                        16

SEQ ID NO: 12        moltype = AA  length = 15
FEATURE              Location/Qualifiers
REGION               1..15
                     note = peptide molecule
source               1..15
                     mol_type = protein
                     organism = synthetic construct
SEQUENCE: 12
GLNVNTLSYG DLAAD                                                         15

SEQ ID NO: 13        moltype = AA  length = 10
FEATURE              Location/Qualifiers
REGION               1..10
                     note = peptide molecule
source               1..10
                     mol_type = protein
                     organism = synthetic construct
SEQUENCE: 13
DGSVVVNKVS                                                               10

SEQ ID NO: 14        moltype = AA  length = 11
FEATURE              Location/Qualifiers
REGION               1..11
                     note = peptide molecule
source               1..11
                     mol_type = protein
                     organism = synthetic construct
SEQUENCE: 14
NTLSYGDLAA D                                                             11

SEQ ID NO: 15        moltype = AA  length = 13
FEATURE              Location/Qualifiers
REGION               1..13
                     note = peptide molecule
VARIANT              1
                     note = MISC_FEATURE - Xaa is absent or is selected from the
                      group consisting of a beta alanine residue,
                      9-amino-3,6-dioxaoctanoic acid, and an acetyl group
SITE                 13
                     note = MISC_FEATURE - Amidated residue (NH2 group)
source               1..13
                     mol_type = protein
                     organism = synthetic construct
SEQUENCE: 15
XHGLNVNTLS YGD                                                           13

SEQ ID NO: 16        moltype = AA  length = 13
FEATURE              Location/Qualifiers
REGION               1..13
                     note = peptide molecule
VARIANT              1
                     note = MISC_FEATURE - X is absent or is selected from the
                      group consisting of a beta alanine residue,
                      9-amino-3,6-dioxaoctanoic acid, and an acetyl group
SITE                 2
                     note = MISC_FEATURE - D-amino acid residue
SITE                 4..11
                     note = MISC_FEATURE - D-amino acid residue
SITE                 13
                     note = MISC_FEATURE - D-amino acid residue
```

| | | |
|---|---|---|
| SITE | 13 | |
| | note = MISC_FEATURE - Amidated residue (NH2 group) | |
| source | 1..13 | |
| | mol_type = protein | |
| | organism = synthetic construct | |
| SEQUENCE: 16 | | |
| XDGYSLTNVN LGH | | 13 |
| | | |
| SEQ ID NO: 17 | moltype = AA   length = 13 | |
| FEATURE | Location/Qualifiers | |
| REGION | 1..13 | |
| | note = peptide molecule | |
| VARIANT | 1 | |
| | note = MISC_FEATURE - X is absent or is selected from the group consisting of a beta alanine residue, 9-amino-3,6-dioxaoctanoic acid, and an acetyl group | |
| SITE | 2 | |
| | note = MISC_FEATURE - D-amino acid residue | |
| SITE | 4..11 | |
| | note = MISC_FEATURE - D-amino acid residue | |
| SITE | 13 | |
| | note = MISC_FEATURE - D-amino acid residue | |
| SITE | 13 | |
| | note = MISC_FEATURE - Amidated residue (NH2 group) | |
| source | 1..13 | |
| | mol_type = protein | |
| | organism = synthetic construct | |
| SEQUENCE: 17 | | |
| XHGLNVNTLS YGD | | 13 |
| | | |
| SEQ ID NO: 18 | moltype = AA   length = 12 | |
| FEATURE | Location/Qualifiers | |
| REGION | 1..12 | |
| | note = peptide molecule | |
| SITE | 1 | |
| | note = MISC_FEATURE - D-amino acid residue | |
| SITE | 12 | |
| | note = MISC_FEATURE - D-amino acid residue | |
| SITE | 12 | |
| | note = MISC_FEATURE - Amidated residue (NH2 group) | |
| source | 1..12 | |
| | mol_type = protein | |
| | organism = synthetic construct | |
| SEQUENCE: 18 | | |
| HGLNVNTLSY GD | | 12 |
| | | |
| SEQ ID NO: 19 | moltype = AA   length = 12 | |
| FEATURE | Location/Qualifiers | |
| REGION | 1..12 | |
| | note = peptide molecule | |
| SITE | 12 | |
| | note = MISC_FEATURE - D-amino acid residue | |
| SITE | 12 | |
| | note = MISC_FEATURE - Amidated residue (NH2 group) | |
| source | 1..12 | |
| | mol_type = protein | |
| | organism = synthetic construct | |
| SEQUENCE: 19 | | |
| HGLNVNTLSY GD | | 12 |
| | | |
| SEQ ID NO: 20 | moltype = AA   length = 12 | |
| FEATURE | Location/Qualifiers | |
| REGION | 1..12 | |
| | note = peptide molecule | |
| SITE | 1 | |
| | note = MISC_FEATURE - D-amino acid residue | |
| SITE | 12 | |
| | note = MISC_FEATURE - Amidated residue (NH2 group) | |
| source | 1..12 | |
| | mol_type = protein | |
| | organism = synthetic construct | |
| SEQUENCE: 20 | | |
| HGLNVNTLSY GD | | 12 |
| | | |
| SEQ ID NO: 21 | moltype = AA   length = 12 | |
| FEATURE | Location/Qualifiers | |
| REGION | 1..12 | |
| | note = peptide molecule | |
| SITE | 12 | |

-continued

```
                        note = MISC_FEATURE - Amidated residue (NH2 group)
source                  1..12
                        mol_type = protein
                        organism = synthetic construct
SEQUENCE: 21
HGLNVNTLSY GD                                                              12

SEQ ID NO: 22           moltype = AA   length = 13
FEATURE                 Location/Qualifiers
REGION                  1..13
                        note = peptide molecule
SITE                    1
                        note = MOD_RES - bAla - Beta-alanine
SITE                    13
                        note = MISC_FEATURE - Amidated residue (NH2 group)
source                  1..13
                        mol_type = protein
                        organism = synthetic construct
SEQUENCE: 22
XHGLNVNTLS YGD                                                             13

SEQ ID NO: 23           moltype = AA   length = 12
FEATURE                 Location/Qualifiers
REGION                  1..12
                        note = peptide molecule
SITE                    1
                        note = MISC_FEATURE - Acetylated residue (Ac group)
SITE                    1
                        note = MISC_FEATURE - D-amino acid residue
SITE                    3..10
                        note = MISC_FEATURE - D-amino acid residue
SITE                    12
                        note = MISC_FEATURE - D-amino acid residue
SITE                    12
                        note = MISC_FEATURE - Amidated residue (NH2 group)
source                  1..12
                        mol_type = protein
                        organism = synthetic construct
SEQUENCE: 23
DGYSLTNVNL GH                                                              12

SEQ ID NO: 24           moltype = AA   length = 12
FEATURE                 Location/Qualifiers
REGION                  1..12
                        note = peptide molecule
SITE                    1
                        note = MISC_FEATURE - Acetylated residue (Ac group)
SITE                    1
                        note = MISC_FEATURE - D-amino acid residue
SITE                    3..10
                        note = MISC_FEATURE - D-amino acid residue
SITE                    12
                        note = MISC_FEATURE - D-amino acid residue
SITE                    12
                        note = MISC_FEATURE - Amidated residue (NH2 group)
source                  1..12
                        mol_type = protein
                        organism = synthetic construct
SEQUENCE: 24
HGLNVNTLSY GD                                                              12

SEQ ID NO: 25           moltype = AA   length = 11
FEATURE                 Location/Qualifiers
REGION                  1..11
                        note = amino acid sequence inverted for peptide molecule
source                  1..11
                        mol_type = protein
                        organism = synthetic construct
SEQUENCE: 25
GLNVNTLSYG D                                                               11
```

METHOD FOR THE TREATMENT OF ALLERGIC RHINITIS

CROSS-REFERENCE TO RELATED APPLICATIONS

The present application is a Continuation of U.S. application Ser. No. 17/751,313 filed May 23, 2022, now issued as U.S. Pat. No. 11,834,478, which is a Continuation of U.S. application Ser. No. 16/476,058 filed Jul. 3, 2019, now issued as U.S. Pat. No. 11,479,585; which is a 35 USC § 371 National Stage application of International Application No. PCT/GB2018/050073 filed Jan. 11, 2018, which claims the benefit under 35 USC § 119 (a) to United Kingdom Patent Application No. 1700555.4 filed Jan. 12, 2017. The disclosure of each of the prior applications is considered part of and is incorporated by reference in the disclosure of this application.

SEQUENCE LISTING

The instant application contains a Sequence Listing which has been submitted electronically in XML file format and is hereby incorporated by reference in its entirety. Said XML copy was created on Apr. 19, 2024, is named 409176-1140C02US_SL.xml and is 46,423 bytes in size.

The present invention relates to methods for the acute treatment of a relapsing-remitting condition, specifically methods using peptides derived from the Mycobacteria tuberculosis derived polypeptide chaperonin 60.1, and the peptide molecules and pharmaceutical compositions for use in such methods.

Heat shock polypeptides are a family of molecules found in all organisms, whose function is to aid the biological processing and stability of biological molecules (Zugel & Kauffman (1999) Role of heat shock polypeptides in protection from and pathogenesis of infectious diseases. *Clin. Microbiol. Rev.* (12) 1:19-39; Ranford et al. (2000) *Chaperonins are cell signalling polypeptides:—the unfolding biology of molecular chaperones.* Exp. Rev. *Mol. Med.,* 15 September, www.ermn.cbcu.cam.ac.uk/).

*Mycobacterium tuberculosis* (*M. tuberculosis*) produces Chaperonin 60.1 (Cpn60.1), a polypeptide that is named based on its amino acid sequence identity to other known chaperonins. Further *M. tuberculosis* chaperonin polypeptides are chaperonin 10 (Cpn10) and chaperonin 60.2 (Cpn60.2). Cpn60.2 exhibits 59.6% amino acid sequence identity and CpN 10 65.6% nucleic acid sequence identity to Cpn60.1.

International Patent Application, Publication Number WO02/040037 discloses pharmaceutical compositions comprising Cpn60.1 from *M. tuberculosis* (MtCpn60.1) and its encoding nucleic acid molecules. This application also discloses a number of specific peptide fragments derivable from the whole length polypeptide. A variety of therapeutic uses for these molecules is also disclosed, including the treatment and/or prevention of autoimmune disorders, allergic conditions, conditions typified by a Th2-type immune response and conditions associated with eosinophilia.

International Patent Application, Publication Number WO2009/106819 discloses a series of novel peptides derivable from MtCpn60.1 including a peptide (designated as "Peptide 4") having an amino acid sequence: DGSVVVNKVSELPAGHGLNVNTLSYGDLAAD (SEQ ID: NO: 1). Peptide 4 exhibits anti-inflammatory activity and has been shown to significantly reduce the recruitment of eosinophils in an animal model of allergic airway inflammation.

A further patent application disclosed certain sub-fragments of SEQ ID: NO 1 which exhibit improved biological activity, in particular an ability to inhibit leukocyte diapedesis. The peptides are particularly suited for development as pharmaceuticals owing to their comparatively short amino acid chain length which renders them convenient to prepare and isolate in high yield.

However, the prior art only discloses the use of such peptides in chronic therapies of inflammatory conditions. Such therapies require continuous dosing of the peptide and the maintenance of detectable levels of the peptide in blood plasma in order for a therapeutic effect to be achieved. This means that patients would need to administer the peptide for extended periods of time, with no respite, providing increased potential for compliance issues and increasing drug burden to the patients. Thus, there is a need for an acute therapy which can be administered at the onset of or during a relapse of a condition, causing remission, but without the need for further continuous dosing to maintain the remission. The present invention is based on the unexpected observation that, in contrast to the previous held convention, chaperonin peptides may be given intermittently in order to obtain a therapeutic effect, for example an anti-inflammatory effect. The observed effect is considered "disease modifying" to the extent that disease symptoms are minimized after an isolated dosing of the desired peptide.

Thus, in a first aspect, the invention provides a method for the acute treatment of a relapsing-remitting condition, the method comprising the step of administering to a subject in need thereof one or more doses of an effective amount of a peptide molecule comprising or consisting of an amino acid sequence selected from one of the group (i) to (xv):

```
(i)
                                       (SEQ ID NO: 1)
DGSVVVNKVSELPAGHGLNVNTLSYGDLAAD;

(ii)
                                       (SEQ ID NO: 2)
XHGLNVNTLSYGD
``` wherein X is absent or is selected from the group consisting of a beta alanine residue, 9-amino-3,6-dioxaoctanoic acid, and an acetyl group; or variants thereof comprising one or more of ii (i) to ii (iii);

ii (i) one or more amino acid residues are in the D conformation, ii (ii) GLNVNTLSYGD is inverted, or ii (iii) the carboxyl terminal amino acid residue is converted to a primary carboxamide group;

```
(iii)
                                       (SEQ ID NO: 3)
DGSVVVNKVSEL-NH2;

(iv)
                                       (SEQ ID NO: 4)
SELPAGHGLNVNTLSYGDLAAD;

(v)
                                       (SEQ ID NO: 5)
SELPAGHGLNVNTLS;
```

-continued (vi)
PAGHGLNVNTLS-NH2; (SEQ ID NO: 6)

(vii)
VVVNKVSELPAGHGLNVNTLSYGDLAAD; (SEQ ID NO: 7)

(viii)
NKVSELPAGHGLNVNTLSYGDLAAD; (SEQ ID NO: 8)

(ix)
PAGHGLNVNTLSYGDLAAD; (SEQ ID NO: 9)

(x)
HGLNVNTLSYGDLAAD; (SEQ ID NO: 10)

(xi)
DGSVVVNKVSELPAGH; (SEQ ID NO: 11)

(xii)
GLNVNTLSYGDLAAD; (SEQ ID NO: 12)

(xiii)
DGSVVVNKVS; (SEQ ID NO: 13)

(xiv)
NTLSYGDLAAD; (SEQ ID NO: 14)

and
(xv) a polypeptide sequence which has more than 85% or 90% or 95% identity to any of
(i) to (xiv) and has a function equivalent to any of (i) to (xiv);
in response to or during a relapse, wherein the method causes remission of the condition.

The invention relates to a method for the acute treatment of a relapsing-remitting condition. The inventors have surprisingly found that one or more initial doses can be administered to provide a long-term therapeutic effect, without the need for continuous or long-term regular administration of a therapeutic agent. The methods of the invention cause disease modification. It is thought that the agents of the invention modify the underlying disease or condition rather than simply treating the symptoms of the disease or condition. The peptides of the invention are disease-modifying agents, i.e they are agents which provide a therapeutic benefit that persists beyond their pharmacokinetic coverage. The term "disease-modifying agent" was originally used in the context of agents for treating rheumatoid arthritis, Disease-modifying antirheumatic drugs, so-called "DMARDs". However, "disease modification" is now used more generally in medicine and pharmaceutical science, and does not simply apply to rheumatoid arthritis. Rather a skilled person is aware that disease modification is a term used in the context of treating a range of conditions. For example, disease modification is also used in relation to treatments for asthma. For example, *Lancet* Respiratory Medicine, "Clinical trial research in focus: do trials prepare us to deliver precision medicine in those with severe asthma?", Brightling (2017), *Vol 5 February* 2017, 92-95, listed as a key finding that "New treatments for asthma need to be more ambitious to achieve complete disease remission, disease modification, and cure." In addition, *The Lancet* Commission: "After asthma: redefining airways diseases", Ian D Pavord et al, Sep. 11, 2017, S0140-6736 (17) 30879-6 lists one of 7 recommendations as to "Move beyond a disease control-based approach for asthma treatment·Direct resources toward primary prevention strategies (asthma prevention) and disease modifying interventions (asthma cure)."

As used herein "treatment" means reducing, alleviating or eliminating one or more symptoms of the condition which is being treated, relative to the symptoms prior to treatment. The term "acute treatment" is used to mean that the peptide is administered at the onset of or during a period of relapse of the condition but that it is not necessary for the peptide to be continuously administered. In particular it may not be necessary for the peptide to be administered during periods of remission of the condition. Thus the "acute treatment" according to the present invention can be distinguished from known methods for the treatment of relapsing-remitting conditions which provide chronic therapy requiring continuous, long-term administration of the pharmaceutical without any breaks in treatment. The provision of an acute treatment provides significant advantages to the patient. Since the peptides of the invention only need to be administered over a short period of time, side effects, for example injection site reactions are reduced. In addition, during periods of remission patients enjoy an improved lifestyle, without the need to remember dosage regimens.

Without being bound by theory, it is understood that the peptides of the invention do not simply affect the symptoms of the condition or disease, but rather they modify the underlying condition or disease itself. Thus administration of the peptide of the invention has a long-term effect.

In one embodiment, remission of the condition is maintained without the need for the administration of further doses of the peptide. It will be noted that the acute treatment may comprise the administration of one or more doses of an effective amount of the peptide molecule at the onset of or during the relapse of the condition. In some cases, administration of one or more doses of the peptide may be required during the remission period. However, continuous administration of an effective amount of the peptide is not required. Preferably, the administration of further doses during remission is not required.

In a particularly preferred embodiment a single dose of the peptide molecule is administered to the subject.

In another embodiment, two or more doses, preferably 3 doses are administered over a short period of time, for example over a period of 1 day, 3 days, 28 days, 56 days or 112 days. The time between dose administration to the subject may be 3 hours, 1 day, 14 days, 28 days or 56 days after the previous dose.

Remission usually comprises the reduction, alleviation or elimination of one or more symptoms of the condition. Typically remission or clinical remission comprises a period with no symptoms associated with the relapsing-remitting disease or a period during which the symptoms associated with the disease have decreased in severity and/or in number. A symptom associated with a condition, disease or disorder includes any clinical or laboratory manifestation associated with the disease or disorder. Clinical remission may therefore be measured according to the relevant scale or remission indicators, different for each disease and well known in the medical field by for example, clinicians and researchers. Conversely, relapse of the condition may be defined as the increase or appearance of one or more symptoms of the condition. It will be understood that the symptoms to be reduced, alleviated or eliminated are dependent on the particular relapsing-remitting condition to be treated. For example, symptoms of asthma may be shortness of breath, difficulty breathing, chest tightness, coughing, reduced lung capacity, trouble sleeping caused by shortness of breath, coughing or wheezing, a whistling or wheezing sound when inhaling, coughing or wheezing attacks that are worsened by a respiratory virus such as cold or flu. Additionally symptoms may include hospitalization, loss of work/school attendance or death.

A reduction or elimination of one or more symptoms is typically a significant reduction or elimination of one or more symptoms as identified by a physician. Symptoms of the relapsing-remitting conditions can be measured and quantified using well-known diagnostic tests. For example, lung function tests such as spirometry and methacholine challenge tests can be used to quantify the symptoms of asthma, using ACQ scores. The ACQ is a simple questionnaire to measure the adequacy of asthma control and change in asthma control which occurs either spontaneously or as a result of treatment. ACQ has a multidimensional construct assessing symptoms (5 items-self-administered) and rescue bronchodilator use (1 item-self-administered), and forced expiratory volume in 1 minute (FEV1) (1 item) completed by clinic staff (Juniper E F, O'Byrne P M, Guyatt G H, Ferrie P J, King D R. Development and validation of a questionnaire to measure asthma control. *Eur Respir J* 1999; 14:902-907).

As well as providing a clinical definition of remission, it is also possible to define a biological or mechanistic definition of remission. In a particularly preferred embodiment the condition is associated with eosinophilia and/or neutrophilia. In this case remission comprises a significant reduction in the number of neutrophils and/or the number of eosinophils trafficking to a site of inflammation in the human or animal subject relative to a control subject who has not been administered the peptide molecule. If the condition is a pulmonary condition, remission comprises a significant reduction in the number of neutrophils and/or the number of eosinophils recruited to the lungs or found within the circulatory system.

Remission may also be associated with a significant reduction in the number of lymphocytes or a significant increase in the number of macrophages in the human subject relative to a control subject. Remission may further be associated with a significant change in the amount of one or more inflammatory markers such as cytokines, for example IL-4, IL-5, IL-10 or IL-13 in the human subject relative to a control subject. Remission may comprise a significant increase in the amount of IL-10 in the human subject relative to a control subject Remission may comprise a significant reduction in the amount of IL-4, IL-5 or IL-13 in the human subject relative to a control subject.

A relapsing-remitting condition is any condition which has one or more periods of relapse, wherein each relapse is followed by a period of remission.

During these symptom free periods or periods of remission, patients do not require quantifiable circulating levels of the therapeutic peptide. In a preferred embodiment remission is maintained when the plasma peptide concentration is below the lower limit of quantification. This limit of quantification may vary depending on the detection method employed. Typically the plasma peptide concentration is undetectable at circulating levels of less than 40 ng/ml, for example less than 30 ng/mL or 20 ng/ml. A typical method for determining the plasma peptide concentration is high resolution accurate mass (HRAM) LC-MS/MS.

In a preferred embodiment remission of the condition is for a period of at least 7 days, for example 14 days, at least 28 days, more preferably at least 6 months after the concentration of the peptide molecule in the plasma of the subject is undetectable.

In another embodiment remission of the condition is for a period of at least 7 days, optionally at least 14 days, optionally at least 28 days, optionally at least 6 months after administration of the final dose of the peptide.

Typically the relapsing-remitting condition is an inflammatory condition. Preferably the condition is selected from the group consisting of asthma, Crohn's disease, allergic inflammatory conditions such as atopic dermatitis and rhinitis, rheumatoid arthritis and inflammatory bowel disease.

A key advantage of the peptide molecules of the invention is that they are effective treatments for conditions with a neutrophil component such as severe asthma, cystic fibrosis, bronchiectasis (including non-CF), pulmonary arterial hypertension, pulmonary fibrosis, and acute respiratory distress syndrome inflammatory bowel disease including ulcerative colitis and Crohn's disease and COPD. Additionally, neutrophil driven diseases can include asthma, attacks of gout, glomerulonephritis, rheumatic fever, collagen-vascular diseases and hypersensitivity reactions and metabolic diseases such as diabetic ketoacidosis, preeclampsia, and uremia, especially with uremic pericarditis. Neutrophil driven collagen disease, Gaucher's disease, Cushing's syndrome, myelofibrosis, neoplastic neutrophilia, polycythemia vera, psoriasis, inflammatory bowel disease. Other examples include Wegeners vasculitis, cystic fibrosis, Sjogrens syndrome, chronic transplant rejection, type 1 diabetes graft versus host disease, thyroiditis, spondyloarthropathy, ankylosing spondylitis, uveitis, and polychondritis or scleroderma.

In an alternative embodiment, the present invention provides the use of a peptide as defined herein when the relapsing-remitting conditions are autoimmune disorders. Examples of autoimmune disorders which may be prevented and/or treated with the peptide molecules of the present invention include autoimmune disorders, such as haemolytic anaemia, thrombocytopenia, pernicious anaemia, Addison's disease, autoimmune diabetes, insulin dependent diabetes mellitus, myasthenia gravis, rheumatoid arthritis, systemic lupus erythematosus, atherosclerosis, autoimmune encephalitis, connective tissue disease, multiple sclerosis (including relapsing multiple sclerosis), autoimmune pulmonary inflammation, Guillain-Barre syndrome, autoimmune thyroiditis, graft-versus-host disease and autoimmune inflammatory eye disease. Preferred autoimmune disorders include rheumatoid arthritis, and systemic lupus erythematosus.

In an alternative embodiment, the present invention provides the use of a peptide as defined herein for the remission of allergic conditions. Examples of allergic conditions and disorders which may be improved or go into remission on treatment with the peptide molecules of the present invention include eczema, atopic dermatitis, allergic rhinitis (hay fever), allergic airways diseases, hyper-eosinophilic syndrome, respiratory diseases characterized by eosinophilic airway inflammation and airway hyper-responsiveness, such as asthma, including allergic asthma and intrinsic asthma, allergic bronchopulmonary aspergillosis, eosinophilic pneumonia, allergic bronchitis bronchiectasis, interstitial lung disease, hyper-eosinophilic syndrome, urticaria, angioedema, erythema multiforme, Stevens-Johnson syndrome, allergic conjunctivitis, atopic keratoconjunctivitis, venereal keratoconjunctivitis and giant papillary conjunctivitis. Preferred allergic disorders and conditions include asthma, allergic rhinitis, and atopic dermatitis. In another aspect the condition involves viral exacerbations of allergic conditions including asthma. In another aspect the condition involves exacerbations associated with bacterial infections.

Preferably, remission comprises the reduction, alleviation or elimination of one or more symptoms of the condition for a period of time which significantly exceeds the plasma pharmacokinetic half-life of the peptide. This typically means a significant reduction in disease severity for a period of time which significantly exceeds the plasma pharmacokinetic half-life of the peptide therapeutic.

The peptides may be used according to the invention when the patient is further administered one or more therapeutic agents or when the peptides are provided in combination with one or more therapeutic agents. The therapeutic agent may be selected from, but not limited to, disease modifying agents, including biological immunomodulators, analgesics, broncodilators, anti-inflammatory agents, anti-allergic drugs, allergen immunotherapeutic agents, antivirals, antibiotics, antibodies, steroids and drugs commonly used in the treatment of relapsing-remitting conditions according to the invention.

Disease modifying agents include for example hydroxychloroquine, sulfasalazine, leflunamide, methotrexate and minocycline and biologics which target TNFalpha, such as abatacept, adalimumab, etanercept, infliximab and golimumab, or immunomodulators such as alemtuzumab, interferon beta-1b, beta interferon-1a dimethyl fumarate, copaxone, natalizumab and teriflunomide. Analgesics include, paracetamol, non steroidal anti-inflammatory drugs such as ibuprofen and aspirin, codeine, tramadol, morphine, amitriptyline, gabapentin and opiates.

Anti-inflammatory agents include leukotriene receptor antagonists, theophylline, selective PDE4 inhibitors such as roflumilast, dual PDE3/4 inhibitors such as RPL 554, low, medium and high dose corticosteroids, via inhalation, subcutaneous, intramuscular, sublingual, intravenous and oral dosing. Antivirals include oseltamivir. Antibiotics include amoxicillin. Antibodies include anti-IgE antibodies (e.g. omaluzimab), antibodies which modify cytokine signaling (e.g. anti-IL-5mab mepoluzimab). Steroids include fluticasone propionate and fluticasone furorate, beclomethasone dipropionate, budesonide, ciclesonide, flunisolide, and mometasone. The use according to the invention when the further one or more therapeutic agents are selected from corticosteroids, anti-leukotrienes, cytokine monoclonal antibodies or theophylline may be preferred. Use when the further agent is a bronchodilator may also be preferred. Preferred bronchodilators include, short acting B2 agonists such as salbutamol, long acting B2 agonists such as salmeterol, formoterol, olodaterol and vilanterol, short acting muscarinic receptor antagonists such as ipratropium bromide and long acting muscarinic receptor antagonists such as aclidinum bromide, tiotropium bromide, and glycopyrronium bromide.

The peptides of the invention are chemically or recombinantly synthesized and have a number of different chemical, structural and functional properties to the full-length chaperonin 60.1.

By "functionally equivalent" peptide is meant any peptide and/or variant or fragment thereof which possesses a function (e.g. biological activity) that is identical or substantially similar to any function displayed by or attributed to one or more of the defined amino acid sequences (i) to (xiv). For example, a peptide consisting of the amino acid sequence defined in (i) reduces trafficking of immune cells such as eosinophils and/or neutrophils to sites of inflammation, permitting its use in the prevention and/or treatment of a variety of diseases and disorders, including asthma, rheumatoid arthritis and inflammatory bowel disease including ulcerative colitis and Crohn's disease. Functional equivalence in respect of a particular biological activity can be measured using conventional models and methods; for example, by measuring inflammogen induced immune cells such as eosinophils or neutrophils, pulmonary influx in sensitized (inflammogen—ovalbumin/house dust mite) or naïve (inflammogen—LPS) animals.

A peptide may have an amino acid sequence which has 80% or more, 90% or more, or 95% or more identity to the sequences (i) to (xiv) above. These peptide molecules may differ by amino acid insertions, deletions, and substitutions, created using, e g., recombinant DNA techniques. Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequence.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

Preferably, amino acid "substitutions" are the result of replacing one amino acid with another amino acid having similar structural and/or chemical properties, i.e., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are preferably in the range of about 1 to 10 amino acids, more preferably 1 to 5 amino acids, such as 1, 2, 3, 4 or 5 amino acids. The variation allowed may be experimentally determined by systematically making insertions, deletions, or substitutions of amino acids in a polypeptide molecule using recombinant DNA techniques or synthetic techniques such as solid phase synthesis and assaying the resulting recombinant variants for biological activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited to synthetic manufacture or for expression, scale up and the like in the host cells chosen for expression.

Fragments of the peptides of the present invention which are capable of exhibiting biological activity are also encompassed by the present invention. Such fragments may be in linear form or they may be cyclized using known methods, for example, as described in H. U. Saragovi, et al., *Bio/Technology* 10, 773-778 (1992) and in R. S. McDowell, et al., *J. Amer. Chem. Soc.* 114, 9245-9253 (1992), both of which are incorporated herein by reference. Such fragments may be fused to carrier molecules such as immunoglobulins for many purposes, including increasing the valency of protein binding sites.

By "identity" is meant the number or percentage (dependent on presentation of the results) of amino acid residues or nucleic acid residues in a candidate sequence that are identical with the amino acid residues or nucleic acid residues of the sequence of interest, after aligning the sequences and introducing gaps, if necessary to achieve maximum percent sequence identity, and not considering any conservative substitutions as part of the sequence identity.

The percentage sequence identity between two polynucleotides or polypeptides may be determined using suitable computer programs, for example the GAP program of the University of Wisconsin Genetic Computing Group and it will be appreciated that percent identity is calculated in relation to polypeptides whose sequence has been aligned optimally. The alignment may alternatively be carried out using the Clustal W program (Thompson et al., (1994) *Nucleic Acids Res.* 22, 4673-80). The parameters used may be as follows: fast pairwise alignment parameters: K-tuple (word) size; 1, window size; 5, gap penalty; 3, number of top diagonals; 5. Scoring method: x percent; multiple alignment parameters: gap open penalty; 10, gap extension penalty; 0.05. Scoring matrix: BLOSUM.

Sequence identity may be determined, e.g., using the Jotun Hein method (Hein, J. (1990) *Methods Enzymol.* 183:626-645). Identity between sequences can also be determined by other methods known in the art, e.g. by varying hybridization conditions.

The peptides of the present invention may be prepared and/or isolated using conventional methods known in the art. For example, by solution or solid phase synthesis using traditional methods or using a solid phase automated synthesizer, for example as described in I. Coin, *Nature Protocols*, 2007, 2, 3247-3256. Preferably, the peptides of the present invention are prepared by Fmoc solid phase synthesis using methods analogous to those described in G. B. Fields and R. L. Noble, Int. *J. Peptide Protein Res.*, 1990, 35 (3), 161-214.

In preferred embodiments of the method, the peptide molecule consists of an amino acid sequence selected from one of the group (a) to(s):

(a) (SEQ ID NO: 1)
DGSVVVNKVSELPAGHGLNVNTLSYGDLAAD (b) (SEQ ID NO: 15)
XHGLNVNTLSYGD-NH2

(c) (SEQ ID NO: 16)
XdGysltnvnlGh-NH2;

(d) (SEQ ID NO: 17)
XhGlnvntlsyGd-NH2;

-continued (e) (SEQ ID NO: 18)
hGLNVNTLSYGd-NH2;

(f) (SEQ ID NO: 19)
HGLNVNTLSYGd-NH2;

(g) (SEQ ID NO: 20)
hGLNVNTLSYGD-NH2;

(h) (SEQ ID NO: 3)
DGSVVVNKVSEL-NH2;

(i) (SEQ ID NO: 4)
SELPAGHGLNVNTLSYGDLAAD;

(j) (SEQ ID NO: 5)
SELPAGHGLNVNTLS;

(k) (SEQ ID NO: 6)
PAGHGLNVNTLS-NH2;

(l) (SEQ ID NO: 7)
VVVNKVSELPAGHGLNVNTLSYGDLAAD;

(m) (SEQ ID NO: 8)
NKVSELPAGHGLNVNTLSYGDLAAD;

(n) (SEQ ID NO: 9)
PAGHGLNVNTLSYGDLAAD;

(o) (SEQ ID NO: 10)
HGLNVNTLSYGDLAAD (p) (SEQ ID NO: 11)
DGSVVVNKVSELPAGH;

(q) (SEQ ID NO: 12)
GLNVNTLSYGDLAAD;

(r) (SEQ ID NO: 13)
DGSVVVNKVS;
and (s) (SEQ ID NO: 14)
NTLSYGDLAAD;

wherein upper case denotes an L-amino acid residue, lower case denotes a D-amino acid residue, X is absent or is selected from the group consisting of a beta alanine residue, 9-amino-3,6-dioxaoctanoic acid, and an acetyl group.

The nomenclature for amino acid and peptide derivatives conforms to IUPAC-IUB rules (*J. Peptide Sci.* 1999, 5, 465-471). D-amino acids are indicated by lower-case abbreviations, e.g. Ala or A for L-alanine, ala or a for D-alanine.

The peptides of the invention preferably consist of from 5 to 50, 5 to 40 amino acid residues, preferably 5 to 35, or 5 to 20 amino acid residues.

In a particularly preferred embodiment the peptide comprises the amino acid sequence DGSVVVNKVSELPA-GHGLNVNTLSYGDLAAD (SEQ ID NO: 1). The peptide is preferably less than 50 amino acid residues in length, most preferably less than 40 residues in length. In a particularly preferred embodiment the peptide consists of the 31 amino acid residue SEQ ID NO: 1.

In a preferred embodiment the isolated or recombinant peptide molecule consists of an amino acid sequence HGLNVNTLSYGD-NH2 (SEQ ID NO: 21) or a functionally equivalent fragment or variant thereof.

In a preferred embodiment the isolated or recombinant peptide molecule consists of an amino acid sequence bAla-HGLNVNTLSYGD-NH2 (SEQ ID NO: 22) or a functionally equivalent fragment or variant thereof.

In another preferred embodiment the isolated or recombinant peptide molecule consists of an amino acid sequence Ac-dGysltnvnIGh-NH2 (SEQ ID NO: 23), Ac-hGInvntl-syGd-NH2 (SEQ ID NO: 24) or a functionally equivalent fragment or variant thereof.

In a further preferred embodiment the present invention provides an isolated or recombinant peptide molecule consisting of an amino acid sequence hGLNVNTLSYGd-NH2 (SEQ ID NO: 18) or a functionally equivalent fragment or variant thereof.

In an additional preferred embodiment the present invention provides an isolated or recombinant peptide molecule consisting of an amino acid sequence HGLNVNTLSYGd-NH2 (SEQ ID NO: 19); or a functionally equivalent fragment or variant thereof.

In a further preferred embodiment provided is isolated or recombinant peptide molecule consisting of an amino acid sequence hGLNVNTLSYGD-NH2 (SEQ ID NO: 20); or a functionally equivalent fragment or variant thereof.

In another preferred embodiment provided is an isolated or recombinant peptide molecule consisting of an amino acid sequence DGSVVVNKVSEL-NH2 (SEQ ID NO: 3); or a functionally equivalent fragment or variant thereof.

In a further aspect the present invention provides a peptide molecule as defined above for use in a method as defined above.

The relapsing-remitting condition may be an autoimmune disorder such as rheumatoid arthritis, or inflammatory bowel disease (IBD).

The peptide molecules and pharmaceutical compositions of the invention can be introduced to cells by "Trojan peptides". These are a class of polypeptides called penetratins which have translocating properties and are capable of carrying hydrophilic compounds across the plasma membrane. This system allows direct targeting of oligopeptides to the cytoplasm and nucleus, and may be non-cell type specific and highly efficient. See Derossi et al. (1998), *Trends Cell Biol* 8, 84-87.

It is understood that the compounds for use in the invention include salts. Metabolites and pro-drugs are also included. The compounds for use according to the invention also include any isotopic derivatives.

The compounds described herein may be formulated for administration in any convenient way. The present invention provides a pharmaceutical composition comprising a peptide molecule as defined above and one or more pharmaceutically acceptable excipients for use in a method as defined above.

The peptide of the invention may be for use in a human or non-human animal, typically a mammal.

Any suitable route of administration can be used. For example, any of oral, topical, parenteral, ocular, rectal, vaginal, inhalation, buccal, sublingual and intranasal delivery routes may be suitable.

Pharmaceutical compositions for parenteral administration may be preferred. The peptide molecules and pharmaceutical compositions of the invention can be administered parenterally, for example, intravenously, intra-arterially, intraperitoneally, intra-thecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art. Subcutaneous administration may be preferred.

Medicaments and pharmaceutical compositions suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The medicaments and compositions may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

The molecules, medicaments and pharmaceutical compositions of the invention can also be administered intranasally or by inhalation and are conveniently delivered for example in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active agent, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a agent of the invention and a suitable powder base such as lactose or starch.

Aerosol or dry powder formulations are preferably arranged so that each metered dose or "puff" contains at least 100 pg or 200 pg of a molecule of the invention for delivery to the patient. It will be appreciated that the overall daily dose with an aerosol will vary from patient to patient, and may be administered in a single dose or, more usually, in divided doses throughout the day.

The peptide molecules and pharmaceutical compositions of the invention can also be delivered orally. The process may employ a natural process for oral uptake of vitamin $B_{12}$ and/or vitamin D in the body to co-deliver proteins and peptides. By riding the vitamin $B_{12}$ and/or vitamin D uptake system, the nucleic acids, molecules and pharmaceutical formulations of the invention can move through the intestinal wall. Complexes are synthesised between vitamin $B_{12}$ analogues and/or vitamin D analogues and the drug that retain both significant affinity for intrinsic factor (IF) in the vitamin $B_{12}$ portion/vitamin D portion of the complex and significant bioactivity of the active substance of the complex.

The peptide molecules and pharmaceutical compositions of the invention will normally be administered by any parenteral route or intranasally, and in some embodiments orally, in the form of a pharmaceutical composition comprising the active ingredient. Depending upon the disorder and patient to be treated, as well as the route of administration, the compositions may be administered at varying doses.

In human therapy, the peptide molecules and pharmaceutical compositions of the invention can be administered alone but will generally be administered in admixture with a suitable pharmaceutical excipient, diluent or carrier selected with regard to the intended route of administration and standard pharmaceutical practice.

Preferably, the pharmaceutical composition of the present invention is a unit dosage containing a daily dose or unit, daily sub-dose or an appropriate fraction thereof, of the active ingredient.

For example, the peptide molecules and pharmaceutical compositions of the invention can be administered orally, buccally or sublingually in the form of tablets, capsules, ovules, elixirs, solutions or suspensions, which may contain flavouring or colouring agents, for immediate-, delayed- or controlled-release applications. The peptide molecules and pharmaceutical compositions of the invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, and glyceryl behenate may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the agents of the invention may be combined with various sweetening or flavouring agents, colouring matter or dyes, with emulsifying and/or suspending agents and with diluents such as water, ethanol, propylene glycol and glycerin, and combinations thereof.

For oral and parenteral administration to human patients, the daily dosage level of the molecules, medicaments and pharmaceutical compositions of the invention will usually be from 200 pg to 100 mg per adult per day administered in single or divided doses.

Thus, for example, the vial, the tablets or capsules of the molecules of the invention may contain from 200 pg to 100 mg of active agent for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

Alternatively, the molecules, medicaments and pharmaceutical compositions of the invention can be administered in the form of a suppository or pessary, or they may be applied topically in the form of a lotion, solution, cream, gel, ointment or dusting powder. The molecules, medicaments and pharmaceutical compositions of the invention may also be transdermally administered, for example, by the use of a skin patch. They may also be administered by the ocular route, particularly for treating diseases of the eye.

For ophthalmic use, the molecules, medicaments and pharmaceutical compositions of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the molecules, medicaments and pharmaceutical compositions of the invention can be formulated as a suitable ointment containing the active agent suspended or dissolved in, for example, a mixture with one or more of the following: mineral oil, liquid petrolatum, white petrolatum, propylene glycol, polyoxyethylene polyoxypropylene agent, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

For veterinary use, the molecules, medicaments and pharmaceutical compositions of the invention are administered as a suitably acceptable formulation in accordance with normal veterinary practice and the veterinary surgeon will determine the dosing regimen and route of administration which will be most appropriate for a particular animal.

Conveniently, the formulation is a pharmaceutical formulation. Advantageously, the formulation is a veterinary formulation.

Advantageously, in the use according to the invention, the daily dosage level will be from 10 pg to 100 mg. Preferably the daily dosage level will be from 20 pg to 50 mg, 20 pg to 10 mg or 20 pg to 8 mg, administered in single or divided doses.

Preferred pharmaceutical formulations include those in which the active ingredient is present in at least 0.000001% up to 5% by weight. That is, the ratio of active ingredient to the other components (i.e. the addition of adjuvant, diluent and carrier) of the pharmaceutical composition is at least 1:99 (e.g. at least 10:90, preferably at least 30:70 and most preferably at least 50:50) by weight.

Preferably, the pharmaceutical composition or the medicament of the invention is formulated to permit administration by at least one route selected from the group comprising or consisting of: intranasal; oral; parenteral; topical; ophthalmic; suppository; pessary; or inhalation routes. Formulations suitable for such administration routes are well known to those in the art of pharmacy and medicine and exemplary formulations are described above and in the accompanying examples.

DESCRIPTION OF FIGURES

Non-limiting examples will now be described with reference to the following figures.

EXAMPLES

Example 1 (House Dust Mite Study)

Figure 1:
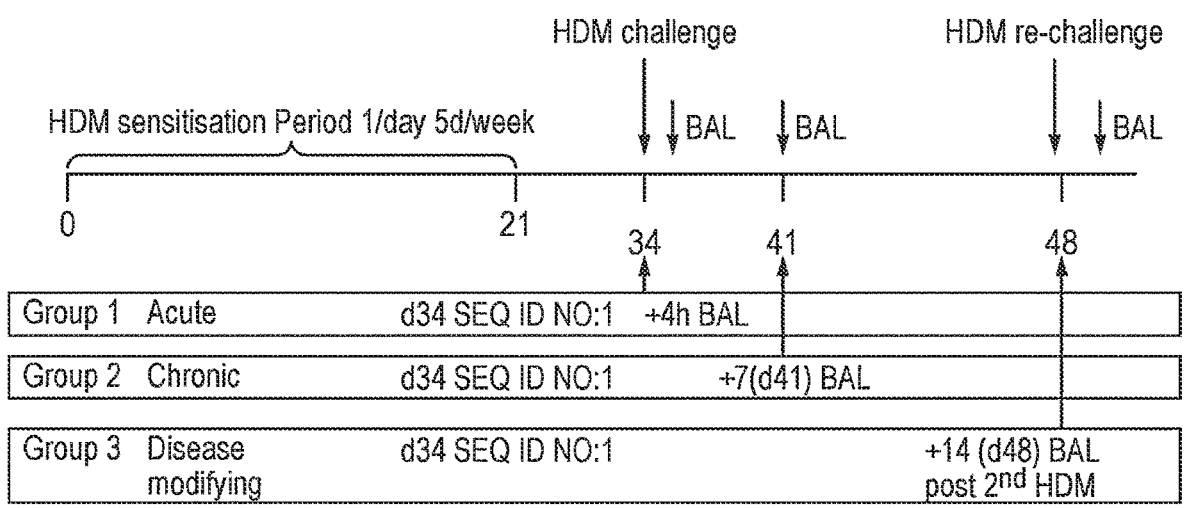
FIG. 1 shows a schematic of the House Dust Mite (HDM) challenge methodology for studying the effects of SEQ ID NO: 1.

The objective of the study was to investigate the inhibitory effects of 3 different concentrations of the peptides in a saline solution on house dust mite (HDM)-induced pulmonary inflammation in Balb/C mice using a 3 week intranasal (i.n.) HDM sensitisation model. Results are shown for SEQ ID NO: 1. This study also looked at time point effects of SEQ ID NO: 1; in addition to 7 day post HDM challenge, a further time point, 4 h post a second HDM challenge (14 days after the first HDM challenge), was investigated to assess the effects of SEQ ID NO: 1 on remission of the allergic response.

The HDM challenge model is a well-established and reliable model where allergens are delivered intranasally (i.n.) to induce airway inflammation.

1. Peptide Synthesis

The peptides were synthesized and isolated according to the following procedures:

Synthesis and purification used automated Fluorenyl-methoxycarbonyl solid phase peptide synthesis (Fmoc SPSS). Peptides were synthesized on Wang resin, derivatized with one of a number of cleavable linkers, using an Fmoc/t-butyl-based solid-phase synthesis strategy.

Temporary N-amino group protection was afforded by the Fmoc-group, with t-butyl ethers being used for protection of tyrosine, serine, and threonine hydroxyl side chains, whereas t-butyl esters protected the side chains of aspartic and glutamic acid residues. Histidine and lysine side chains were protected as their N-trityl and N-Boc derivatives, respectively, cysteine as its S-trityl derivative and arginine guanidine moiety as its Pbf derivative.

Upon completion of the synthesis, peptides were cleaved from the solid support, with removal of side chain protecting groups, by treatment with trifluoroacetic acid (TFA) containing triisobutylsilane and water as scavengers. After removal of TFA and scavengers by evaporation and trituration in diethyl ether, peptide purification was performed by reversed-phase preparative HPLC, followed by lyophilization. The purified product was subsequently analyzed by reverse-phase HPLC and by mass spectrometry.

2. Experimental Protocol

Method

A 3 week sensitisation and challenge model was applied where n=90 female Balb/C mice of approximately 6-8 weeks of age, approximately 20-25 g at start of study were used.

Following 11 days' acclimatisation all mice received 25 µg (total protein) HDM delivered i.n. 5 days/week for 3 weeks. HDM sensitisation was carried out each day of dosing and all intranasal dosing was performed where the mice were lightly anaesthetised using isoflurane. Two weeks after the final HDM sensitisation dose all mice received a single 50 µL i.n. dose of a saline solution of the peptide or saline (0.9% w/v Sodium Chloride) vehicle solution. For SEQ ID NO: 1, dose solutions were 0.02 µg/kg, 0.2 µg/kg and 2 µg/kg. 15 minutes post peptide or saline vehicle dose all mice received a single 50 µL challenge administered i.n. of saline (0.9% w/v Sodium Chloride) or 100 µg HDM.

Some groups of animals received a second 50 µL i.n. administered dose of either saline or HDM 100 µg dose four weeks post sensitisation. Animals were then euthanised 4 hrs post second challenge (corresponding to 14 days post dosing).

All mice were euthanised by intraperitoneal (i.p.) overdose (0.2 mL) of Sodium Pentobarbatone (200 mg/mL). Death was confirmed by cervical dislocation.

Post Mortem Sample Collection
BAL Fluid

The lungs were lavaged via the trachea with 1 mL of BAL (bronchoalveolar lavage) fluid. Samples were placed on wet ice (4° C.) and a differential cell count using a Sysmex XT2000i vet cell analyser was performed before the BAL sample was centrifuged at 1300 rcf for 7 min. A 200 µL BAL supernatant sample was put in a polypropylene U bottom 96 well plate and frozen at −20° C. for subsequent cytokine analysis using a standard MSD protocol.

Data Analysis

Data analysis was performed using Graphpad PRISM 6. The statistical tests applied to determine statistical significance were analysis of variance (ANOVA) followed by a post-hoc test or an unpaired T-test.

3. Results

BAL Cell Influx—Day Time Point

Figure 2:
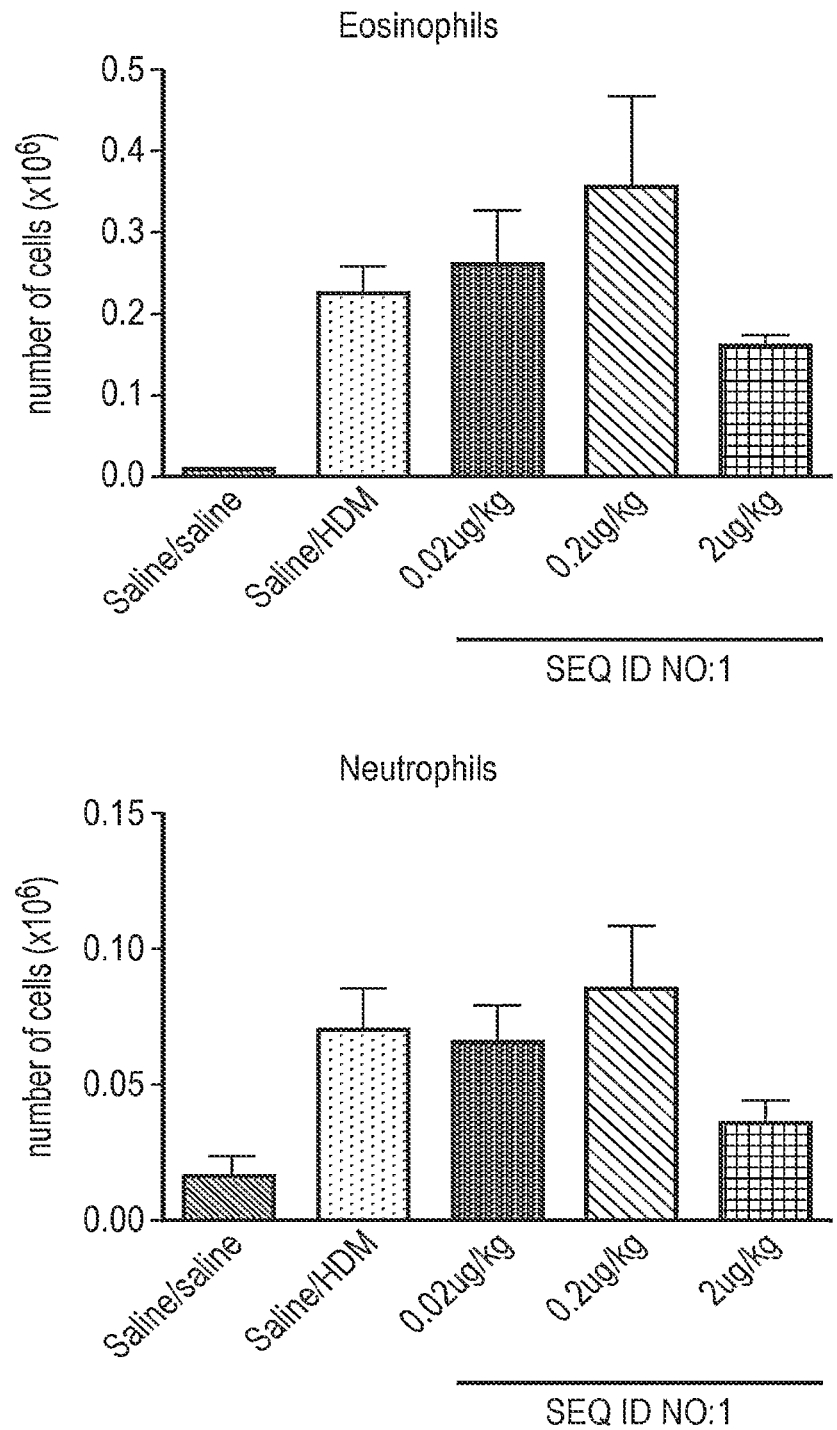
FIG. 2 shows the effects of SEQ ID NO: 1 on lung cell recruitment in female Balb/c mice sensitised with a 3 week HDM treatment at the 7 day time point (7 days post initial challenge with HDM). The number of eosinophils and neutrophils were measured in the following groups: saline, saline/HDM, 0.02 µg/kg SEQ ID NO: 1/HDM, 0.2 µg/kg SEQ ID NO: 1/HDM and 2 µg/kg/HDM SEQ ID NO: 1. Details of the statistical analysis are specified in the figure.

Analysis of cell infiltrate showed an increased level of neutrophils and eosinophils in all HDM treated mice compared to saline/saline group. SEQ ID NO:1 2 µg/kg treated animals showed a decreased level of neutrophils and eosinophils compared to saline/HDM although not statistically significant (FIG. 2).

Figure 3:
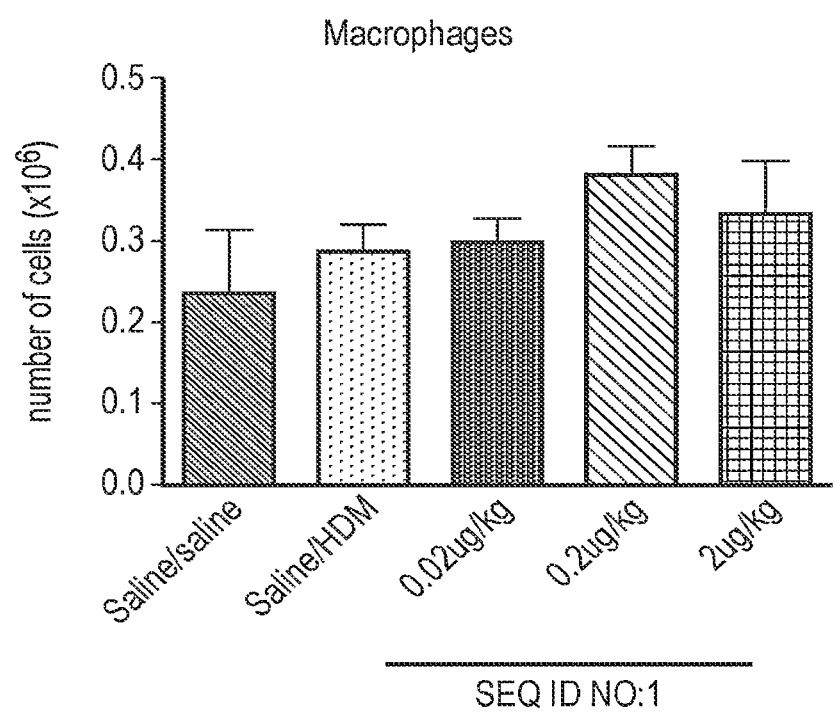
FIG. 3 shows the effects of SEQ ID NO: 1 on lung cell recruitment in female Balb/c mice sensitised with a 3 week HDM treatment at the 7 day post dosing time point. There is trend to an increase in macrophage recruitment into the lungs associated with the treatment groups.

Analysis also shows a trend to an increase of infiltrated macrophages associated with the SEQ ID NO:1 treated groups (FIG. 3)

BAL Cell Influx—14 Day Time Point

SEQ ID NO:1 2 µg/kg treated animals showed a significantly decreased level of neutrophils, eosinophils and lymphocytes compared to saline/HDM.

Eosinophil, neutrophil and lymphocyte cell influx levels were significantly higher for animals given saline/HDM when compared saline/saline via all dosing routes.

Figure 4:
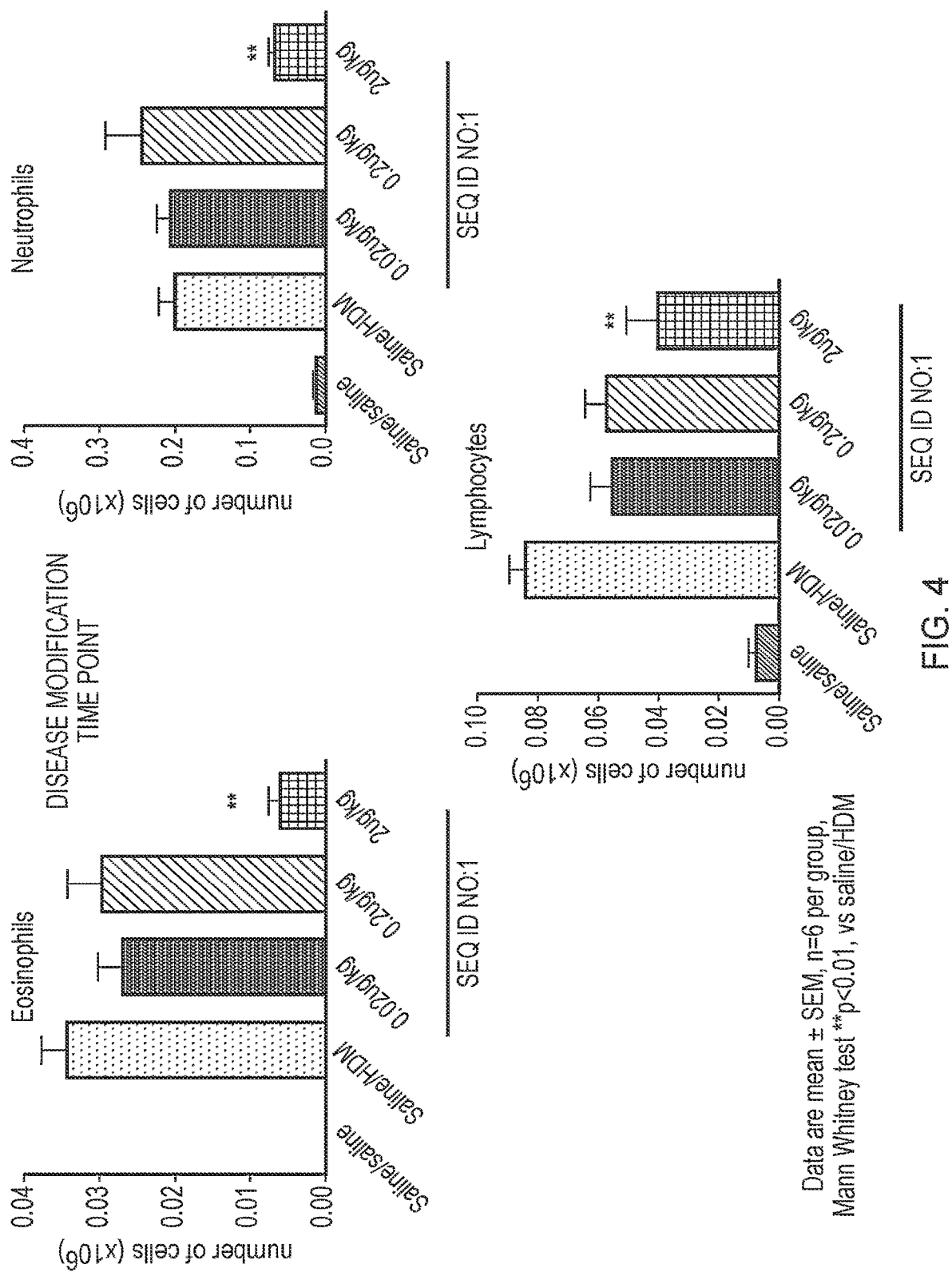
FIG. 4 shows the effects of SEQ ID NO: 1 on lung cell recruitment in female Balb/c mice sensitised with a 3 week HDM treatment at the 14 day time point (4 hrs post second challenge with HDM), corresponding to a disease modification time point. The number of eosinophils, neutrophils and lymphocytes were measured in the following groups: saline, saline/HDM, 0.02 µg/kg SEQ ID NO: 1/HDM, 0.2 µg/kg SEQ ID NO: 1/HDM and 2 µg/kg/HDM SEQ ID NO: 1. Details of the statistical analysis are specified in the figure.

Animals given SEQ ID NO:1 2 µg/kg, showed significantly lower levels of neutrophils, eosinophils and lymphocytes (FIG. 4) when compared to those given saline/HDM administered i.n.

BAL Cytokine Release

Figure 5:
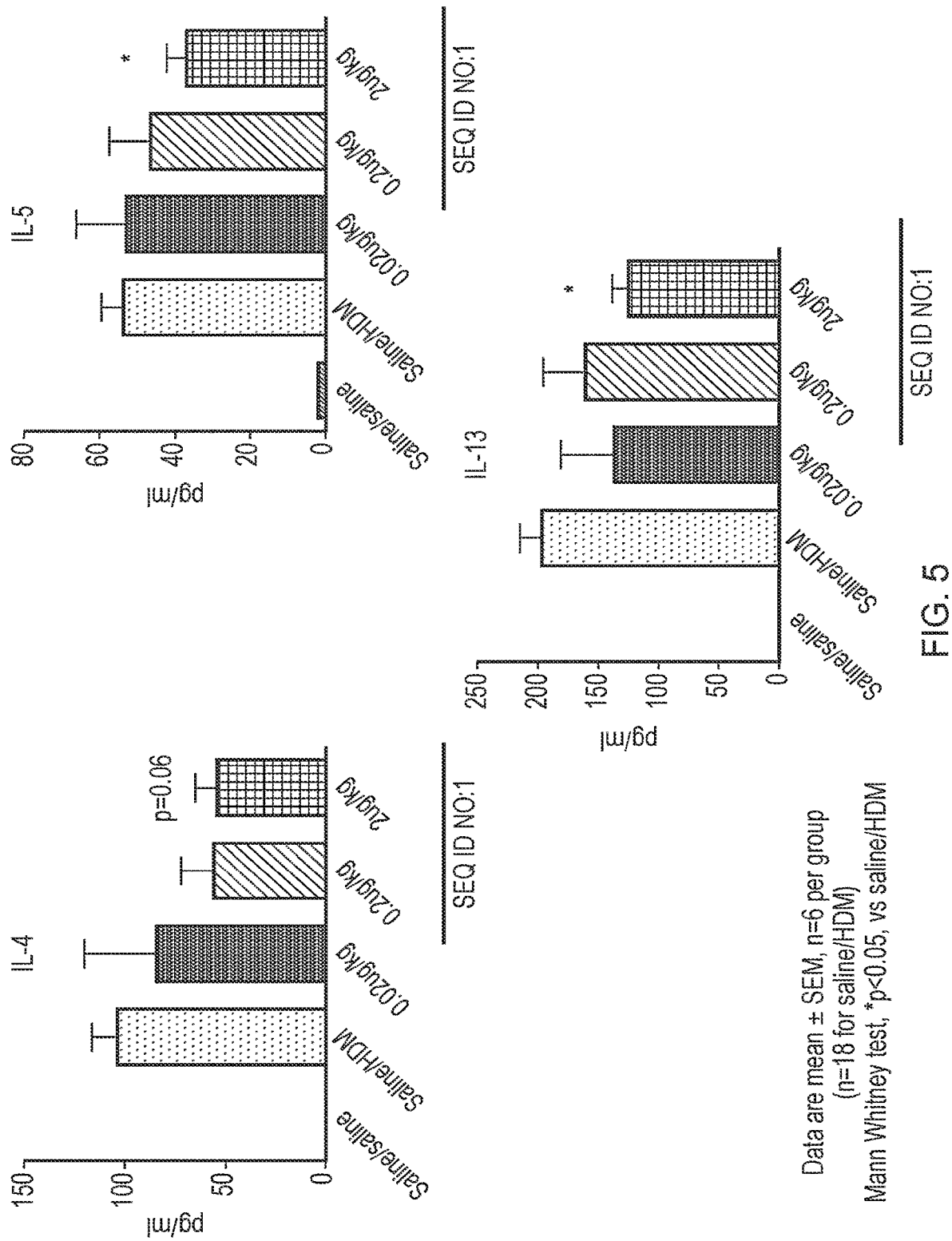
FIG. 5 shows the effects of SEQ ID NO:1 on allergy related cytokine levels in the bronchoalveolar lavage at the disease modification time point (14 days post dosing) in the HDM study. Data refer to SEQ ID NO:1 given i.n. at 0.02 µg/kg, 0.2 µg/kg and 2 µg/kg. Details of the statistical analysis are specified in the figure.

SEQ ID NO:1 2 µg/kg showed a significant inhibition of the levels of IL-4, IL-5 and IL-13 compared to saline/HDM at 14 days time point (FIG. 5).

Figure 6:
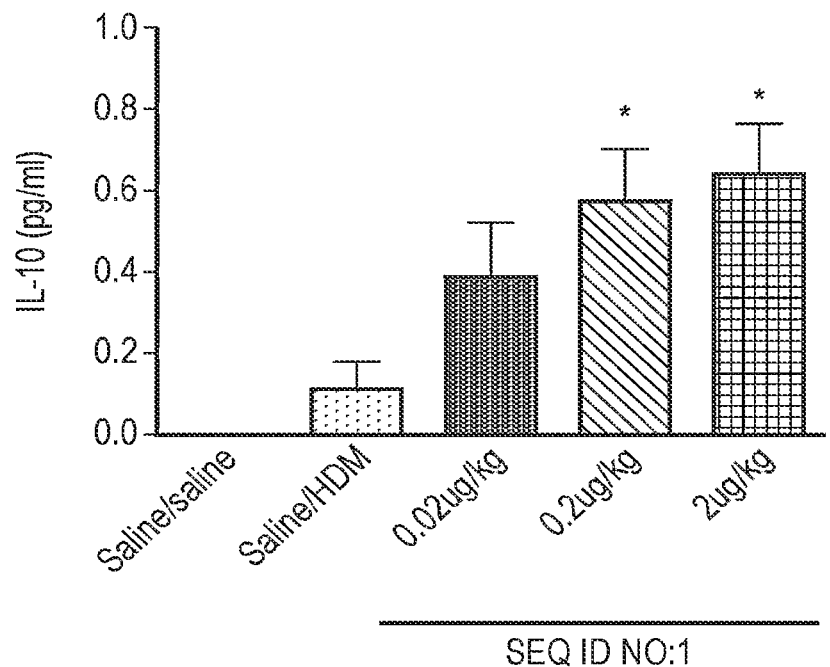
FIG. 6 show the effects of SEQ ID NO: 1 on the anti-inflammatory cytokine IL-10 levels in the bronchoalveolar lavage at 7 days post dosing. This could be associated with the increase in macrophage recruitment shown in FIG. 3 and reflect the promotion with SEQ ID NO: 1 of a pro-resolving anti-inflammatory immune profile. Details of the statistical analysis are specified in the figure.

SEQ ID NO:1 showed a significant dose response release of the anti inflammatory cytokine IL-10 compared to saline/HDM at 7 days time point (FIG. 6).

4. Conclusion

Animals responded to the second HDM challenge and a statistically significant difference was seen between positive and negative control animals. Statistically significant inhibition of BAL eosinophil, neutrophil and lymphocyte influx was seen with the highest dose of SEQ ID NO: 1 (2 µg/kg/HDM) compared to animals that received saline/HDM at 4 hrs post second HDM challenge, the 14 day post dosing time point.

A trend to an increased macrophage influx was seen with SEQ ID NO:1 treated groups compared to animals that received saline/HDM at the 7 day time point. At this time point, SEQ ID NO:1 treated animals showed a dose related increase of the anti-inflammatory cytokine IL-10 in the BAL. IL-10 can be released from macrophages. These data put together suggest a transition to a pro-resolving anti-inflammatory phenotype that could partly explained the 14 day time point data.

Allergy related Th2-cytokines in the BAL 14 days post dosing and 4 h post challenge, IL-4, IL-5 and IL-13 were inhibited by SEQ ID NO:1 2 µg/kg in comparison with the saline/HDM group.

These results show that a single dose of the peptide (shown here for SEQ ID NO: 1) provides a long term effect regardless of circulating levels of peptide no longer being present.

Example 2 (Ovalbumin Study)

Figure 7:
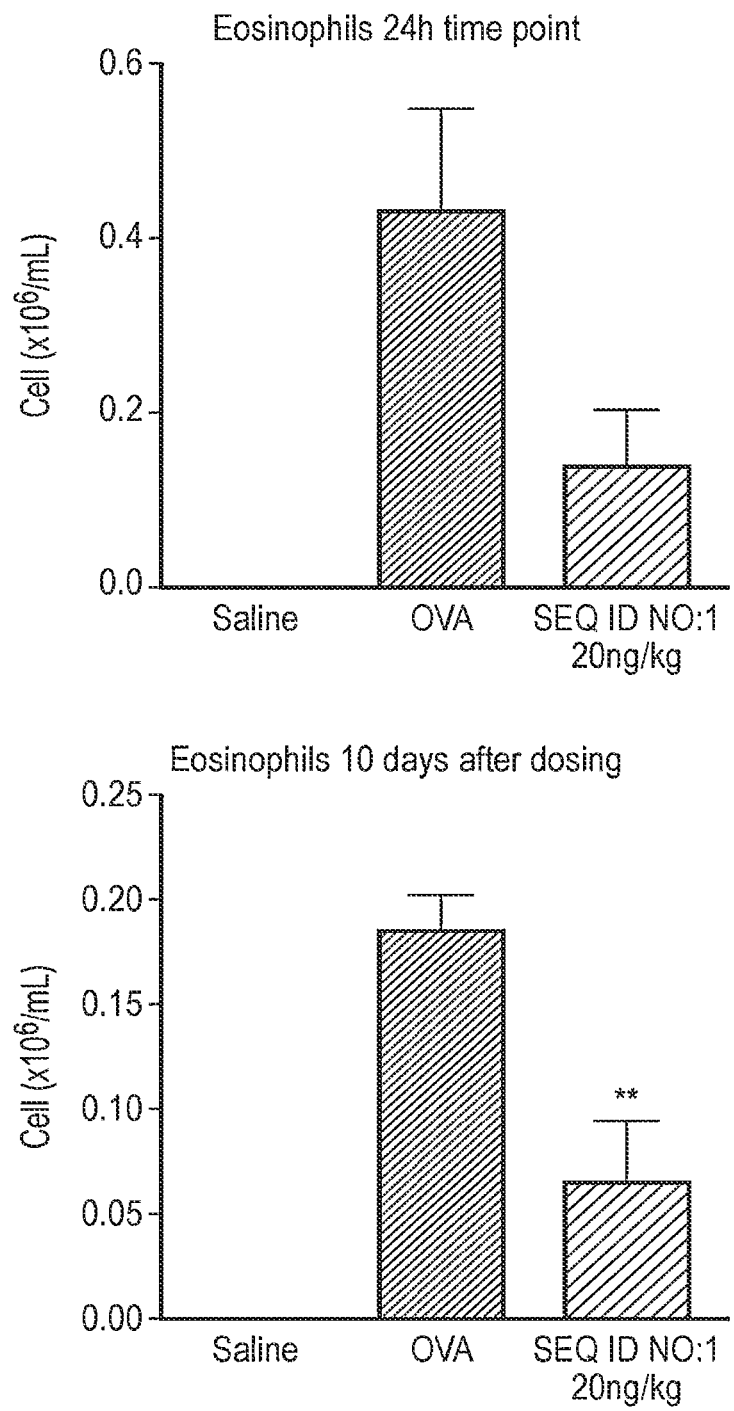
FIG. 7 shows the effects of intravenous SEQ ID NO:1 on eosinophil infiltration into the lung 24 hours after OVA challenge and 24 h after OVA-re challenge, 10 days post dosing. SEQ ID NO: 1 has been used at the dose of 20 ng/kg before each OVA challenge in Balb/c mice sensitised with a week of allergen treatment.
Figure 8:
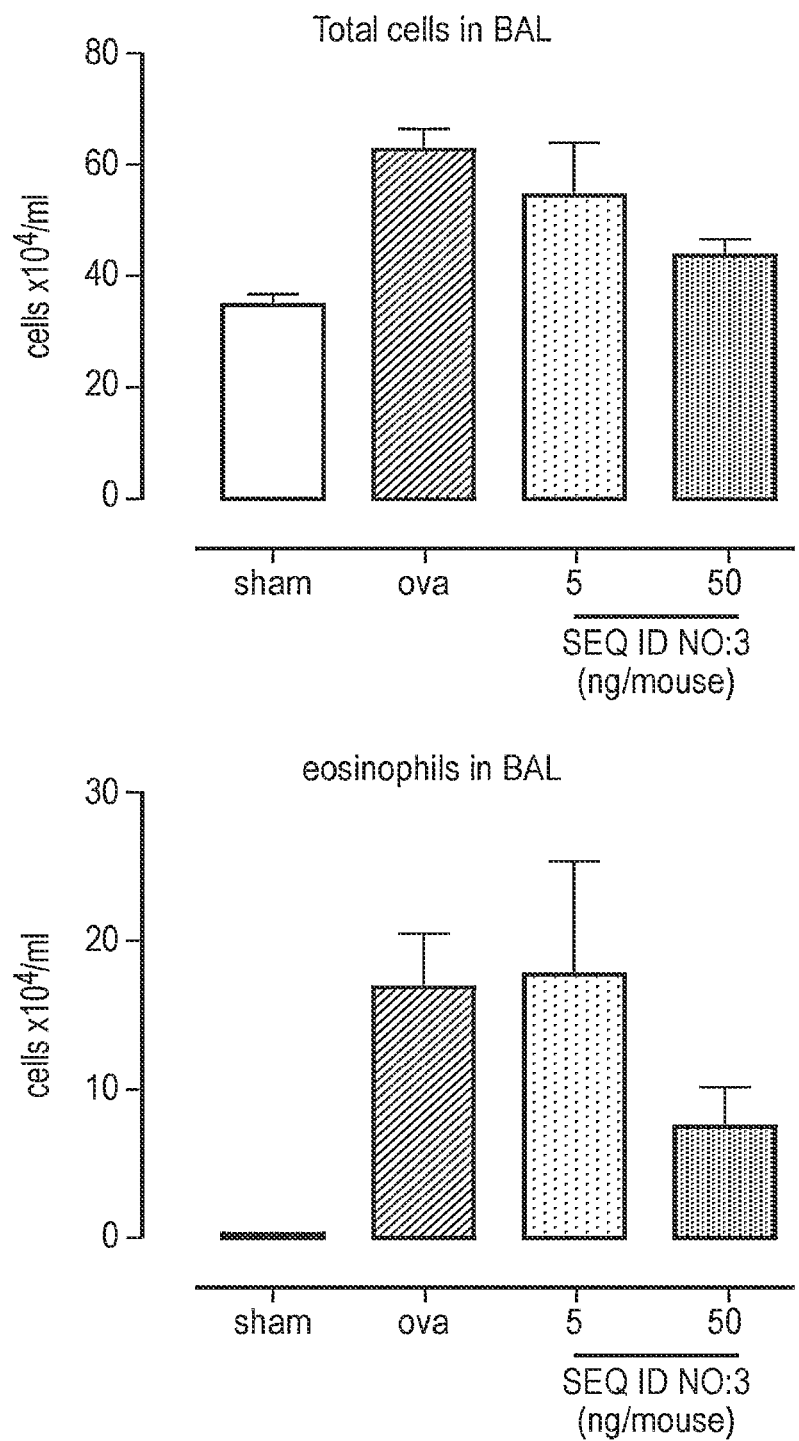
FIG. 8 shows the effects of intranasal SEQ ID NO:3 (5 and 50 ng/mouse) on cell recruitment into the lung after ovalbumin allergen challenge in ovalbumin sensitised mice. Total number of cells recruited and differential counts for eosinophils are shown.

FIGS. 7 and 8 demonstrate the inhibition of allergic inflammation by administration of intravenous SEQ ID NO:1 and intranasal SEQ ID NO: 3 in the mouse ovalbumin model, respectively.

Methods:

In this study, female BALB/c mice were immunized intra-peritoneally with 30 µg of chicken egg albumin absorbed to a saturated solution of aluminium hydroxide (2.5 mg/ml). Controls received aluminium hydroxide only. One week later (day 7) the injection of OVA was repeated. On day 15, all animals were challenged with an aerosolised solution of ovalbumin (3%) for 25 minutes, once daily for 3 consecutive days. SEQ ID NO:1 was diluted in sterile saline and given intravenously 25 µl/mouse, at 20 ng/kg, 10 minutes before each ovalbumin challenge in a total of 3 treatments. In another set of experiments, SEQ ID NO:3 was diluted in sterile saline and given intranasally, at concentrations of 5 and 50 pg/mouse, 10 minutes before each ovalbumin challenge in a total of 3 treatments. Controls received vehicle only.

Ten days after the last OVA challenge, animals that had received SEQ ID NO:1 were re-challenged with OVA for further 3 consecutive days. No treatment with SEQ ID NO: 1 was involved in this phase (FIG. 7).

Mice were euthanized with an overdose of urethane (25% solution i.p.) 24 hours post-challenge and a cannula was inserted into the exposed trachea and three 0.5 ml aliquots of saline were injected into the lungs and removed as broncholaveolar lavage (BAL) fluid. From the BAL fluid, an aliquot (50 µl) was added to 50 µl of haemolysis solution (Turk's solution, Fluka, UK). The total number of cells in the lavage was counted with an improved Neubauer haemocytometer. For differential cell counts, cytospin preparations were prepared from aliquots of BAL fluid (100 µL) centrifuged at 1000 rpm for 1 min using a Shandon Cytospin 2 (Shandon Southern Instruments, Sewickley, PA, USA) at room temperature. Cells were stained with Diff Quick (DADE Behring, Germany) and a total of 100 cells were counted to determine the proportion of neutrophils, eosinophils and monocytes using standard morphological criteria.

Results and Conclusions:

The total number of cells quantified in BAL fluid obtained from OVA-challenged mice 24 h following last ovalbumin (OVA) challenge was significantly higher compared to sham mice and this was reflected by a significantly greater number of eosinophils recruited to the airways in OVA-challenge mice. The intensity of the inflammatory response was significantly reduced in animals treated intravenously with SEQ ID NO:1 before each OVA challenge (FIG. 7).

Ten days after the last OVA challenge, animals were re-challenged with OVA for further 3 consecutive days. No treatment with SEQ ID NO: 1 was involved in this phase. Results show that 10 days after the last OVA challenge, the number of eosinophils in the lung in response to OVA has decreased. Treatment with SEQ ID NO: 1 was efficient in inhibiting the recruitment of eosinophils during this late phase regardless of the fact that circulating levels of peptide were no longer detectable (FIG. 7).

FIG. 8 shows the effects of intranasal doses of SEQ ID NO:3 in the OVA model 24 h post last allergen challenge. The intensity of the inflammatory response, in terms of both total number of cells and eosinophil number, was significantly reduced in animals treated intranasally with 50 ng/mouse of SEQ ID NO:3 before each OVA challenge.

Example 3 (Effect of SEQ ID NO:1 in IL-10 Release from LPS Estimulated Macrophages)

Figure 9:
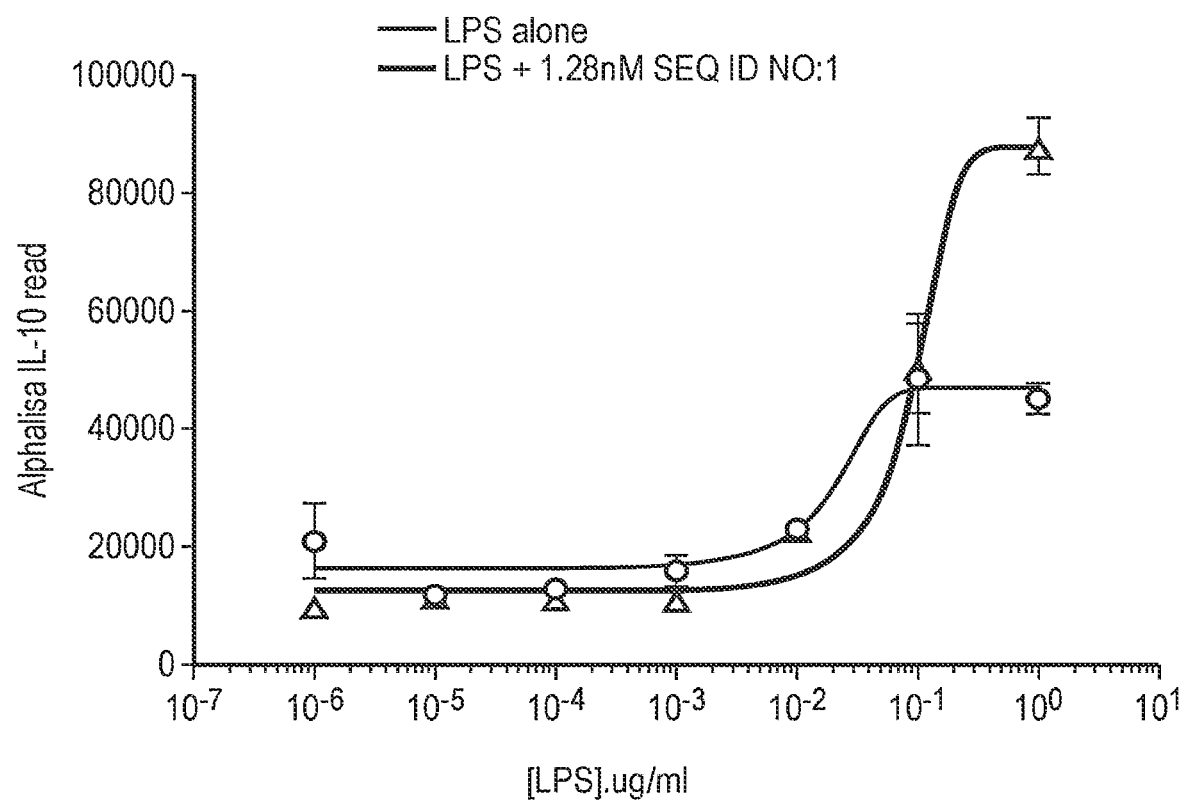
FIG. 9 show the effect of SEQ ID NO:1 potentiating the LPS stimulated IL-10 secretion in human macrophages.

FIG. 9 demonstrates potentiation of IL-10 secretion in LPS stimulated macrophages by SEQ ID NO:1.
Methods:
THP-1 monocytic human cells were differenciated into macrophages with 50 nM phorbol myristate acetate for 48 hrs on a 96 well plate (100K cells/well).
Macrophages were stimulated with increasing concentrations of bacterial lipopolysaccharide (LPS $10^{-6}$-10 µg/ml) in the presence or absence of SEQ ID NO:1 (1 nM). 30 µl of cell media was sampled at 6 hours after LPS stimulation and an IL-10 alphaLISA was run to measure the release of IL-10.
Results and Conclusions:
LPS stimulated the release of IL-10 from THP-1 differenciated macrophages. Treatment with SEQ ID NO:1 (1 nM) potenciated the release of IL-10 at the top LPS doses (1-10 µg/ml; FIG. 9)

Example 4 (Affymetrix Microarray Analysis from Lung Tissue Samples)

Figure 10:
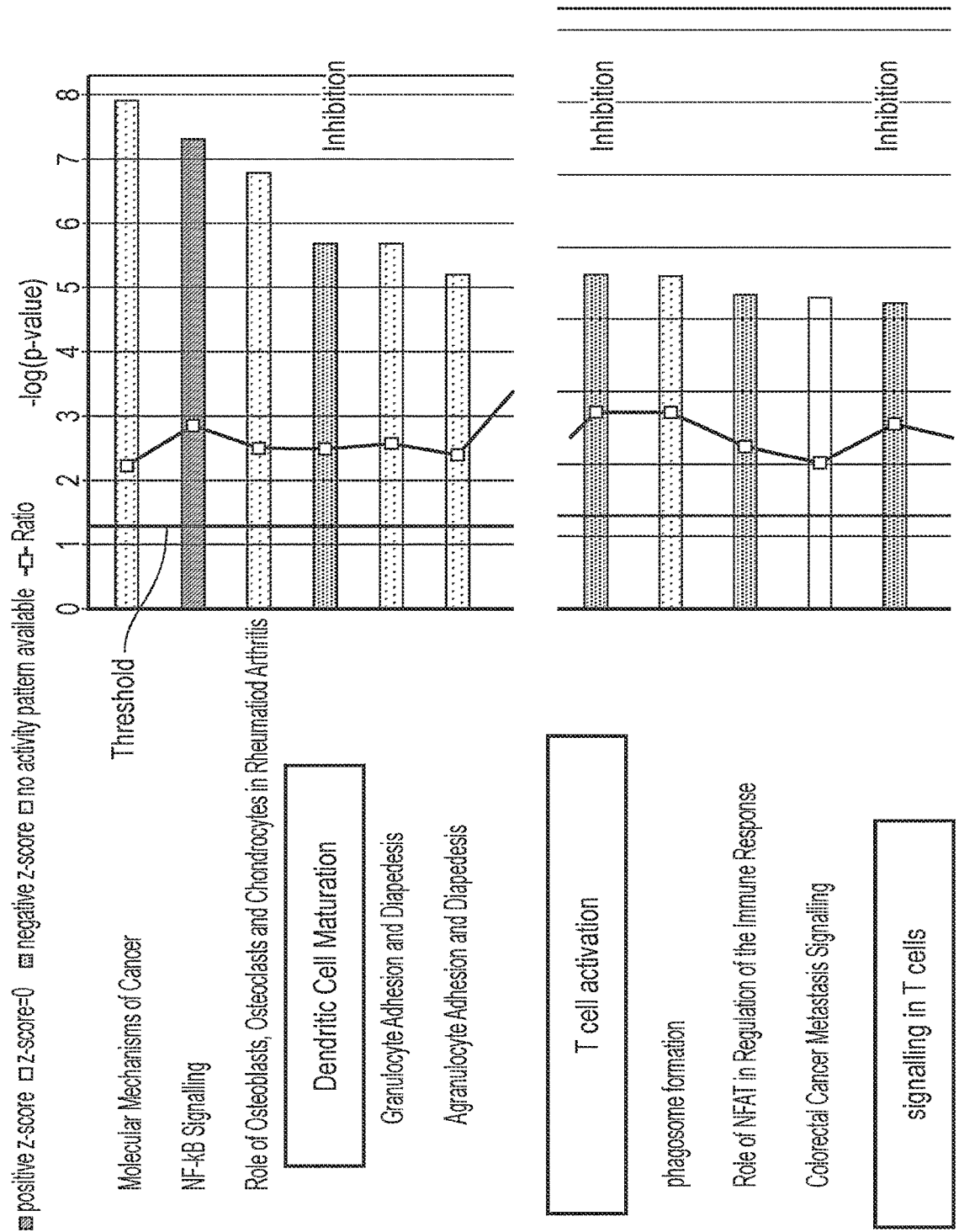
FIG. 10 show evidence that relate the mechanism of action of SEQ ID NO:1 with the maturation of dendritic cells and T cell maturation/development.

FIG. 10 shows the results of an Affymetrix microarray analysis evaluation of lung tissues from the HDM study in Example 1 that suggest that SEQ ID NO:1 is related to dendritic cell maturation and T cell activation/development.
Methods
25 mouse lung tissue FFPE (formalin fixed paraffin embedded) samples from the Example 1 study exposed to one of four treatments (saline, SEQ ID NO:1 0.02 µg\kg, SEQ ID NO:1 2 µg\kg or positive control fluticasone furoate) at either 4 hours or 7 days after stimulation by house dust mite (HDM, 100 µg) were analysed. A single saline sample of each time point was included as vehicle control with no HDM stimulation.

RNA was extracted from these samples and quality of each sample was assessed and found to be in line with other FFPE samples and as expected. Ample RNA was obtained from samples for progression to cDNA generation. 29 cDNAs were generated using Nugen Ovation® FFPE WTA System.

cDNA passed QC typical for FFPE and was progressed to labelling and hybridisation to GeneChip® Mouse Genome 430 2.0 Arrays.
Results and Conclusions
Results were analysed blind by two independent bioinformatic groups and their conclusions were similar, namely that the mechanism of action of SEQ ID NO:1 is related to dendritic cell maturation and T-cell activation and development (FIG. 10).

Example 5 (Effect of SEQ ID NO:1 on Gene Expression Associated to Dendritic Cell Maturation)

Figure 11:
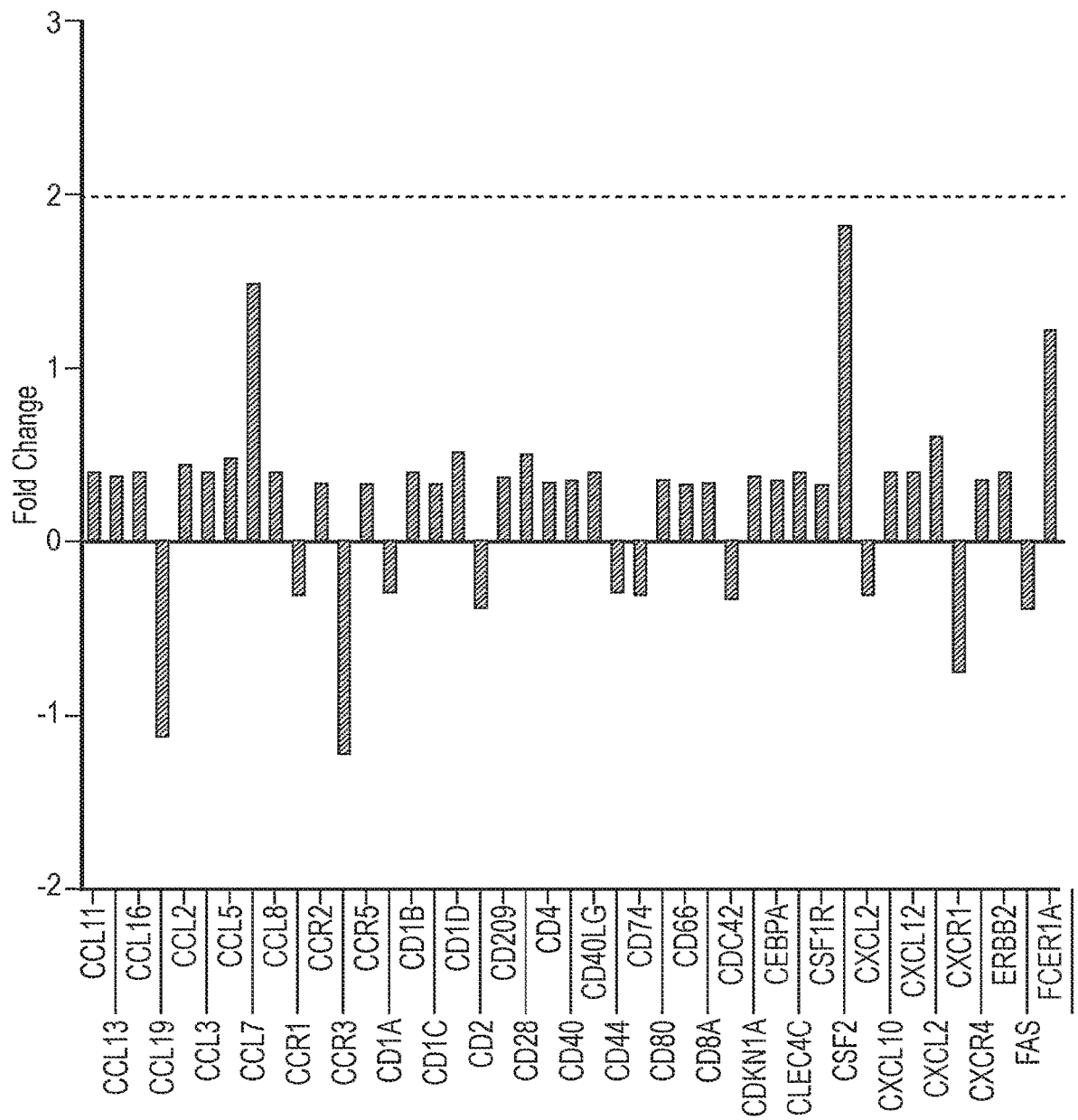
FIG. 11 shows the effect of SEQ ID NO:1 in attenuating the suppression of IL-10 gene expression associated with dendritic cell maturation, once more relating SEQ ID NO:1 mechanism of action with the expression/release of anti-inflammatory cytokine IL-10. Expression changes of more than two fold are considered significant.
Figure 11:
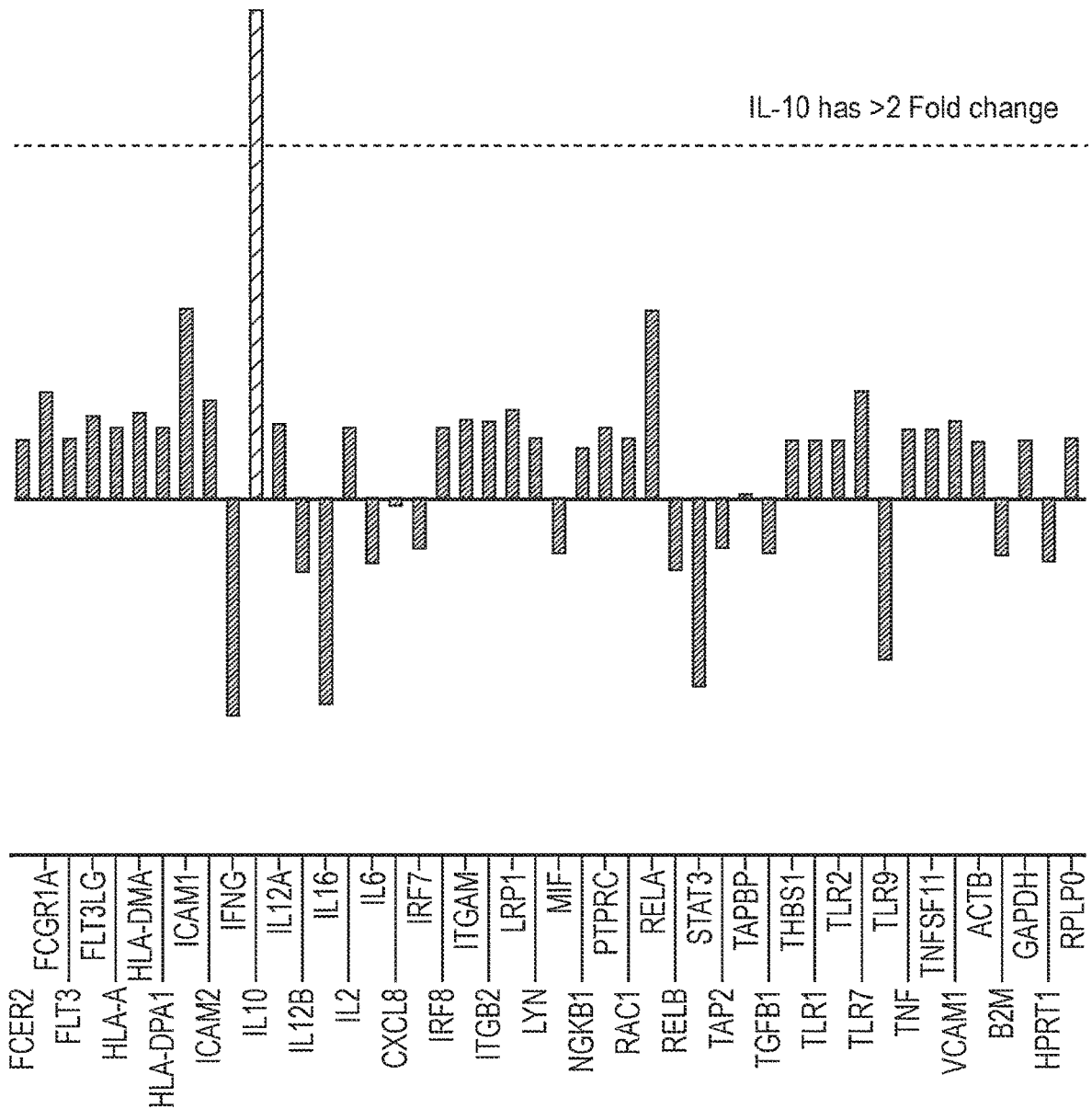

FIG. 11 shows how SEQ ID NO:1 attenuates the suppression of IL-10 gene expression associated with dendritic cell maturation after LPS/IFNγ stimulation.
Methods
CD14+ monocytes were isolated from the blood of 3 healthy donors and differentiated into Immature dendritic cells (iDCs) by treating with GM-CSF and IL4 for 5 days +/− SEQ ID NO:1 (400 nM, 0.04 nM). Phenotype of iDCs was confirmed by flow cytometry and they were further differentiated in mature dendritic cells (mDCs) with LPS (1 µg/ml) and IFN-γ (IU/ml) treatment.
Samples from all three donors (Blank; vehicle+LPS/IFNγ; SEQ ID NO: 1 400 ng/ml+LPS/IFNγ; SEQ ID NO:1 0.04 ng/ml+LPS/IFNγ), 12 in total, were run on a Human Dendritic Cell & Antigen Presenting Cell RT2 Profiler Array (APC Array) that looks for changes in >85 relevant genes.
Results and Conclusions
LPS/IFNγ treatment suppressed the expression of several genes particularly IL-10. Treatment with SEQ ID NO:1 400 ng/ml managed to significantly attenuate the LPS/IFNγ suppression of the IL-10 gene (FIG. 11)

The invention claimed is:

1. A method for the acute treatment of the symptoms of allergic rhinitis, the method comprising the step of:
   (a) administering to a subject in need thereof an effective amount of a peptide molecule comprising an amino acid sequence as set forth in SEQ ID NO:1, or having more than 95% identity to the amino acid sequence as set forth in SEQ ID NO:1, in response to or during a relapse, wherein the acute treatment method causes remission of the symptoms of allergic rhinitis in the subject, and
   (b) stopping the administration of the peptide molecule upon remission of the symptoms of allergic rhinitis.

2. The method of claim 1, wherein the peptide molecule is less than 50 amino acid residues in length.

3. The method of claim 1, wherein the peptide molecule is less than 40 amino acid residues in length.

4. The method of claim 1, wherein the peptide molecule consists of the amino acid sequence of SEQ ID NO:1.

5. The method of claim 1, wherein the remission comprises reduction, alleviation or elimination of one or more symptoms of atopic dermatitis or allergic skin hypersensitivity.

6. The method of claim 1, wherein the remission comprises reduction, alleviation or elimination of one or more symptoms of allergic rhinitis for a period of time which significantly exceeds a plasma pharmacokinetic half-life of the peptide molecule.

7. The method of claim 1, wherein the remission is maintained when a plasma concentration of the peptide molecule is below a lower limit of quantification.

8. The method of claim 7, wherein the plasma concentration is below the lower limit of quantification at circulating levels of less than 20 ng/ml.

9. The method of claim 7, wherein the remission of the symptoms of allergic rhinitis is for a period of at least 7 days after the plasma concentration is below the lower limit of quantification.

10. The method of claim 1, wherein the remission of the symptoms of allergic rhinitis is for a period of at least 7 days after administration of a final dose of the peptide molecule.

11. The method of claim 10, wherein the remission of the symptoms of allergic rhinitis is for a period of at least 14 days after administration of the final dose of the peptide molecule.

12. The method of claim 11, wherein the remission of the symptoms of allergic rhinitis is for a period of at least 28 days after administration of the final dose of the peptide molecule.

13. The method of claim 12, wherein the remission of the symptoms of allergic rhinitis is for a period of at least 6 months after administration of the final dose of the peptide molecule.

14. The method of claim 1, wherein the remission of the symptoms of allergic rhinitis is maintained without the need for the administration of a further dose of the peptide.

15. The method of claim 1, wherein the remission comprises a significant change in the amount of one or more inflammatory markers in the subject relative to a control subject.

16. The method of claim 1, wherein the remission comprises a significant increase in the amount of IL-10 in the subject relative to a control subject.

17. The method of claim 1, wherein the level of one or more of TNF-alpha, IL-1b, IFN-gamma, IL-4, IL-5, IL-6, IL-10, IL-13, IL-17, IL-23, KC (CCL-1), Eotaxin (CCL-11), TARC (CCL-17) and/or MDC (CCL-22) are decreased following administration of SEQ ID NO:1 as compared to prior to administration.

18. The method of claim 1, wherein the subject is further administered one or more additional therapeutic agents.

19. The method of claim 18, wherein the one or more therapeutic agents is selected from the group consisting of disease modifying agents, analgesics, anti-inflammatory agents, anti-allergic drugs, allergen immunotherapeutic agents, antivirals, antibiotics, antibodies and steroids.

20. The method of claim 15, wherein the one or more inflammatory markers are cytokines.

21. The method of claim 20, wherein the cytokines are selected from the group consisting of: IL-4, IL-5, IL-10, and IL-13.

* * * * *